United States Patent
Periana et al.

(10) Patent No.: US 10,858,301 B2
(45) Date of Patent: Dec. 8, 2020

(54) DIRECT OXIDATION OF OLEFINS TO OXYGENATED SPECIES

(71) Applicants: The Scripps Research Institute, La Jolla, CA (US); Hyconix, Inc., Chicago, IL (US)

(72) Inventors: Roy A. Periana, Jupiter, FL (US); Brian G. Hashiguchi, Naperville, IL (US); Michael M. Konnick, Aurora, IL (US)

(73) Assignees: The Scripps Research Institute, La Jolla, CA (US); Hyconix, Inc., Chicago, IL (US)

( * ) Notice: Subject to any disclaimer, the term of this patent is extended or adjusted under 35 U.S.C. 154(b) by 0 days.

(21) Appl. No.: 16/616,626

(22) PCT Filed: May 25, 2018

(86) PCT No.: PCT/US2018/034717
§ 371 (c)(1),
(2) Date: Nov. 25, 2019

(87) PCT Pub. No.: WO2018/218186
PCT Pub. Date: Nov. 29, 2018

(65) Prior Publication Data
US 2020/0095183 A1    Mar. 26, 2020

Related U.S. Application Data

(60) Provisional application No. 62/654,119, filed on Apr. 6, 2018, provisional application No. 62/654,133, filed on Apr. 6, 2018, provisional application No. 62/511,173, filed on May 25, 2017.

(51) Int. Cl.
| | | |
|---|---|---|
| C07C 29/50 | (2006.01) | |
| C07C 29/132 | (2006.01) | |
| C07C 5/50 | (2006.01) | |
| C07C 31/20 | (2006.01) | |

(52) U.S. Cl.
CPC .............. *C07C 5/50* (2013.01); *C07C 29/132* (2013.01); *C07C 29/50* (2013.01); *C07C 31/202* (2013.01); *C07C 31/205* (2013.01); *C07C 2523/18* (2013.01); *C07C 2531/04* (2013.01)

(58) Field of Classification Search
CPC ......... C07C 5/50; C07C 29/132; C07C 29/50; C07C 51/12; C07C 51/44
USPC .......................................................... 564/463
See application file for complete search history.

(56) References Cited

U.S. PATENT DOCUMENTS 4,112,241 A  *  9/1978  Okano ................... C07C 67/05
                                                       560/246
4,508,653 A      4/1985  Goel

FOREIGN PATENT DOCUMENTS

| DE | 108969 A1 | 10/1974 |
| RU | 2219156 C2 | 12/2003 |
| RU | 2599828 C2 | 10/2010 |
| WO | WO 2014/130987 A1 | 8/2014 |
| WO | WO 2015/021126 A1 | 2/2015 |

OTHER PUBLICATIONS

Hashiguchi et al., Designing Catalysts for Functionalization of Unactivated C—H Bonds Based on the CH Activation Reaction, *Accounts of Chemical Rese*, 45(6): 885-898 (Jun. 19, 2012).
European Patent Office, International Search Report and the Written Opinion in International Application No. PCT/US2018/034706 (dated Jul. 23, 2018).
European Patent Office, International Search Report and the Written Opinion in International Application No. PCT/US2018/034698 (dated Sep. 6, 2018).
European Patent Office, International Search Report and the Written Opinion in International Application No. PCT/US2018/034717 (dated Oct. 24, 2018).
Russian Patent Office, Office Action and Search Report in Russian Patent Application No. 2019143401 (dated Apr. 7, 2020).

* cited by examiner

*Primary Examiner* — Yong L Chu
(74) *Attorney, Agent, or Firm* — Leydig, Voit & Mayer, Ltd.

(57) ABSTRACT

Provided is a process for oxidizing an alkene. The process comprises contacting an alkene, and either an oxidizing electrophile comprising a main group element in oxidized form or an oxidant and a reduced form of the oxidizing electrophile, in a liquid medium comprising an oxygen acid and optionally one or more additives selected from a non-oxidizable liquid, a salt additive, a Lewis acid, and water, to provide an oxygenate and a reduced form of the oxidizing electrophile. The process optionally further comprises separating the oxygenate and the reduced form of the oxidizing electrophile. The oxygenate can be further hydrolyzed to form an alcohol, diol, or polyol.

23 Claims, 7 Drawing Sheets

M = As, Sb, or Bi, n = 3, z = 4
M = Te or Se, n = 4, z = 5
M = Sn, n = 2, z = 3

| Entry | Substrate | Oxidant | [Oxidant] (mM) | Oxidant Conversion | Liquid Species | Liq. Species (%/vol) | Additive | [Additive] (mM) | Temp. (°C) | Time (h) |
|---|---|---|---|---|---|---|---|---|---|---|
| 1 | Ethylene | Na[Sb(OH)$_6$] | 100 | N/A | TFAH | N/A | TFA$_2$O | 600 | 180 | 3 |
| 2 | Ethylene | C$_6$F$_5$I(TFA)$_2$ | 100 | N/A | TFAH | N/A | TFA$_2$O | 100 | 100 | 1 |
| 3 | Ethylene | [Sb(OMe)$_5$]$_2$ | 50 | 50 | TFAH | N/A | TFA$_2$O | 2360 | 25 | 0.75 |
| 4 | 1-Hexene | C$_6$F$_5$I(TFA)$_2$ | 100 | 100 | 1,3-(CF$_3$)$_2$-Benzene | N/A | TFAH | 1000 | 100 | 1 |
| 5 | 1-Hexene | Pb(OAc)$_4$ | 100 | N/A | 1,3-(CF$_3$)$_2$-Benzene | N/A | TFAH | 1000 | 100 | 1 |
| 6 | 1-Hexene | Tl(TFA)$_3$ | 100 | N/A | 1,3-(CF$_3$)$_2$-Benzene | N/A | TFAH | 1000 | 100 | 1 |
| 7 | 1-Hexene | Tl(TFA)$_3$ | 100 | N/A | Nitrobenzene | N/A | TFAH | 1000 | 100 | 1 |
| 8 | 1-Hexene | Tl(TFA)$_3$ | 100 | N/A | Nitrobenzene | N/A | TFAH | 1000 | 100 | 1 |
| 9 | N-Allyl-phthalimide | C$_6$F$_5$I(TFA)$_2$ | 100 | 100 | 1,3-(CF$_3$)$_2$-Benzene | N/A | TFAH | 1000 | 150 | 1 |
| 10 | N-Allyl-phthalimide | Tl(TFA)$_3$ | 100 | N/A | 1,3-(CF$_3$)$_2$-Benzene | N/A | TFAH | 1000 | 100 | 1 |
| 11 | 1,5-Hexadiene | C$_6$F$_5$I(TFA)$_2$ | 100 | 100 | 1,3-(CF$_3$)$_2$-Benzene | N/A | TFAH | 1000 | 100 | 1 |

FIG. 7A

| Entry | Substrate | Oxidant | [Oxidant] (mM) | Oxidant Conversion | Liquid Species | Liq. Species (%/vol) | Additive | [Additive] (mM) | Temp. (°C) | Time (h) |
|---|---|---|---|---|---|---|---|---|---|---|
| 12 | 3-Nitrostyrene | $C_6F_5I(TFA)_2$ | 100 | 85 | 1,3-$(CF_3)_2$-Benzene | N/A | TFAH | 1000 | 100 | 1 |
| 13 | 3-Nitrostyrene | $Tl(TFA)_3$ | 100 | N/A | 1,3-$(CF_3)_2$-Benzene | N/A | TFAH | 1000 | 100 | 1 |
| 14 | 3-Nitrostyrene | $Pb(OAc)_4$ | 100 | N/A | 1,3-$(CF_3)_2$-Benzene | N/A | TFAH | 1000 | 100 | 1 |
| 15 | 1-Hexene | $Sb(OAc)_3 / H_2O_2$ | 90 | N/A | Sulfolane | N/A | AcOH / $Ac_2O$ | 1000/400 | 25 | 1 |
| 16 | 1-Hexene | $Sb(OAc)_3 / H_2O_2$ | 90 | N/A | Sulfolane / Nitrobenzene | 50:50 | AcOH / $Ac_2O$ | 1000/400 | 25 | 1 |
| 17 | 4-trifluoromethyl styrene | $Tl(TFA)_3$ | 100 | N/A | 1,3-$(CF_3)_2$-Benzene | N/A | TFAH | 1000 | 100 | 1 |
| 18 | 4-trifluoromethyl styrene | $C_6F_5I(TFA)_2$ | 100 | 85 | 1,3-$(CF_3)_2$-Benzene | N/A | TFAH | 1000 | 100 | 1 |
| 19 | 3,5-bis(trifluoromethyl) styrene | $C_6F_5I(TFA)_2$ | 100 | 15 | 1,3-$(CF_3)_2$-Benzene | N/A | TFAH | 1000 | 100 | 1 |

FIG. 7B

| Entry | Major Product | % Major Product | Minor Product | % Minor Product | Total (% Yield) |
|---|---|---|---|---|---|
| 1 | Et(TFA)$_2$ | 5 | — | — | 5 |
| 2 | Et(TFA)$_2$ | 99 | — | — | 99 |
| 3 | Et(TFA)$_2$ | 56 | — | — | 56 |
| 4 | 1,2-Hex(TFA)$_2$ | 100 | — | — | 100 |
| 5 | 1,2-Hex(TFA)$_2$ | 60 | — | — | 60 |
| 6 | 1,2-Hex(TFA)$_2$ | 40 | — | — | 40 |
| 7 | 1,2-Hex(TFA)$_2$ | 33 | — | — | 33 |
| 8 | 1,2-Hex(TFA)$_2$ | 34 | 1,2-Hex(OAc)$_2$ | 6 | 40 |
| 9 |  | 50 | — | — | 50 |
| 10 |  | 52 | — | — | 52 |
| 11 |  | 18 | — | — | 18 |
| 12 |  | 53 | — | — | 53 |

| Entry | Major Product | % Major Product | Minor Product | % Minor Product | Total (% Yield) |
|---|---|---|---|---|---|
| 13 | 3-nitrophenylacetaldehyde | 14 | 1-(3-nitrophenyl)-1,2-bis(TFA) | 5 | 19 |
| 14 | 3-nitrophenylacetaldehyde | 10 | 1-(3-nitrophenyl)-1,2-bis(TFA) | 4 | 14 |
| 15 | 1,2-Hex(OAc)$_2$ | 38 | — | — | 38 |
| 16 | 1,2-Hex(OAc)$_2$ | 46 | — | — | 46 |
| 17 | 4-(trifluoromethyl)phenylacetaldehyde | 18 | 1-(4-(trifluoromethyl)phenyl)-1,2-bis(TFA) | 4 | 22 |
| 18 | 1-(4-(trifluoromethyl)phenyl)-1,2-bis(TFA) | 62 | — | — | 62 |
| 19 | 1-(3,5-bis(trifluoromethyl)phenyl)-1,2-bis(TFA) | 12 | — | — | 12 |

FIG. 7D

DIRECT OXIDATION OF OLEFINS TO OXYGENATED SPECIES

CROSS-REFERENCE TO RELATED APPLICATIONS

This patent application is a U.S. national phase of International Patent Application No. PCT/US2018/034717, filed May 25, 2018, which claims the benefit of U.S. Provisional Patent Application 62/654,133, filed Apr. 6, 2018, U.S. Provisional Patent Application 62/654,119, filed Apr. 6, 2018, and U.S. Provisional Patent Application 62/511,173, filed May 25, 2017, the disclosures of which are incorporated herein by reference in their entireties for all purposes.

BACKGROUND OF THE INVENTION

Glycols (i.e., diols) are large volume chemicals widely utilized for the production of substances, such as polymers and lubricants. Although glycols are commonly used in many commercial and industrial applications, efficient and low-cost techniques for glycol production are currently underdeveloped in the chemical industry.

Two of the largest volume glycols are ethylene and propylene glycols. The chemical industry generally produces these glycols from hydrolysis of the corresponding oxides, as shown in Eq. A and Eq. B in FIG. 1. This common technique is problematic, however, because it is capital-intensive (i.e., requires two separate plants for producing the epoxide and then producing the glycol) and introduces all of the dangers associated with producing epoxides (e.g., formation of peroxides). In addition, this technique requires an excess of water during the reaction in order to suppress formation of higher glycols (e.g., dipropylene glycol and tripropylene glycol). The separation of water from the product is energy intensive.

Another technique used to produce glycols involves the Halcon process. In this process, ethylene is treated with a Te/Br/$O_2$/HOAc system to generate a diacetate, which is then subsequently hydrolyzed to a glycol. Major problems with this process are that it results in significant corrosion requiring expensive, specialized metallurgy and that significant quantities of undesirable brominated byproducts are produced. These byproducts make it difficult to produce high purity glycol product.

Non-halide and non-epoxide based techniques have also been utilized for the conversion of olefins to glycols. These techniques are based on the use of $TlX_3$ and $O_sO_4$. While these techniques do not involve halides or epoxides, key problems still remain, primarily because these techniques can suffer from increased toxicity and high cost.

Therefore, there is a need for a new, inexpensive process based on the use of low-toxicity or non-toxic materials. Ideally, this process would avoid the use of epoxide intermediates and the presence of halides.

BRIEF SUMMARY OF THE INVENTION

The invention provides a process for oxidizing an alkene, comprising, consisting essentially of, or consisting of: (a) contacting an alkene, and (i) an oxidizing electrophile comprising a main group element in oxidized form, or (ii) an oxidant and a reduced form of the oxidizing electrophile, in a liquid medium comprising an oxygen acid and optionally one or more additives selected from a non-oxidizable liquid, a salt additive, a Lewis acid, and water, to provide an oxygenate and a reduced form of the oxidizing electrophile; and (b) optionally separating the oxygenate and the reduced form of the oxidizing electrophile.

BRIEF DESCRIPTION OF THE DRAWING

FIGS. 7A-7B are tables of exemplary reaction conditions for the procedure outlined in Example 4. FIGS. 7C-7D are tables of exemplary results for the procedure outlined in Example 4.

DETAILED DESCRIPTION OF THE INVENTION

The invention provides a process for oxidizing an alkene, comprising, consisting essentially of, or consisting of: (a) contacting an alkene, and (i) an oxidizing electrophile comprising a main group element in oxidized form, or (ii) an oxidant and a reduced form of the oxidizing electrophile, in a liquid medium comprising an oxygen acid and optionally one or more additives selected from a non-oxidizable liquid, a salt additive, a Lewis acid, and water, to provide an oxygenate and a reduced form of the oxidizing electrophile; and (b) optionally separating the oxygenate and the reduced form of the oxidizing electrophile.

The effectiveness of the process, described herein, is best viewed in terms of the oxidizing electrophile's ability to react selectively with a functionalized or unfunctionalized alkene to form an oxygenate (e.g., a derivative of a glycol), which is ultimately hydrolyzed to form a glycol (i.e., diol). The oxygenate can optionally be separated from the reduced form of the oxidizing electrophile, before the oxygenate is hydrolyzed to provide the glycol. Products generated from the direct oxidation of an alkene are less reactive than the corresponding alkene; moreover, the oxygen-containing groups (e.g., —OY) of the oxygenate are electron-withdrawing, thereby deactivating the oxygenate towards further oxidation. This oxidative process is advantageous because it generates products with high selectivity.

Figure 1:
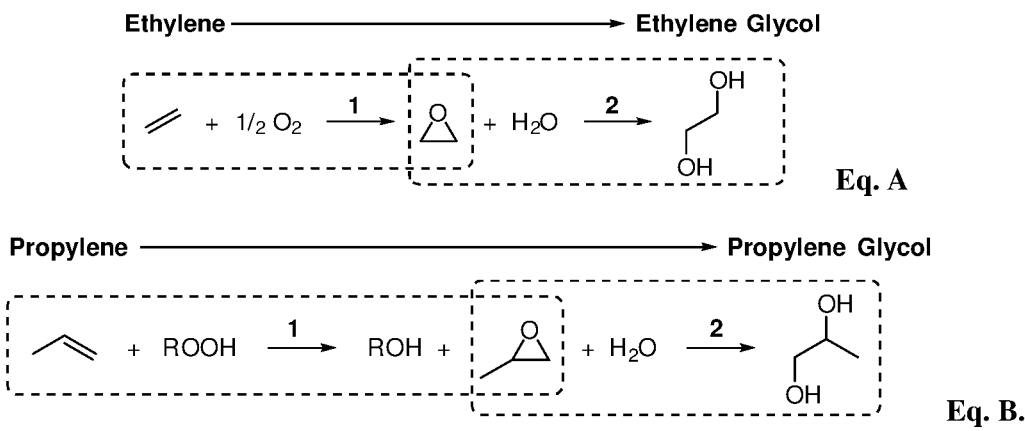
FIG. 1 provides commercially known methods of producing ethylene glycol (Equation A) and propylene glycol (Equation B).
Figure 2:
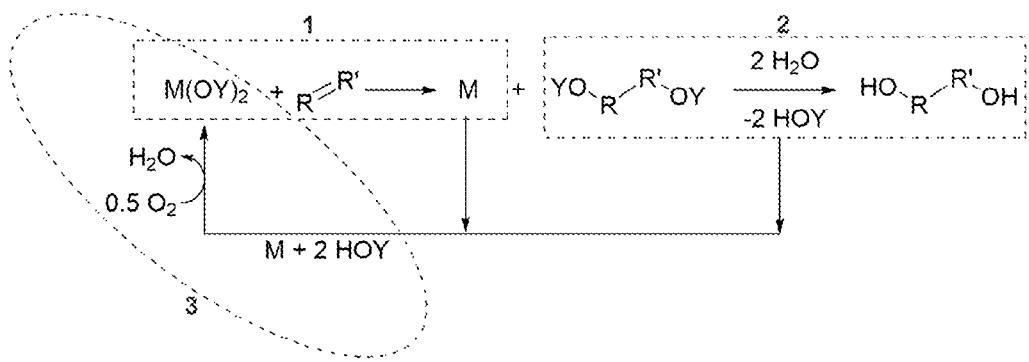
FIG. 2 provides an illustrative process for the conversion of hydrocarbons to alcohols with $O_2$.

A single step alternative to current technologies that could replace multiple technologies would be highly advantageous. A key advantage of the technology described herein and exemplified in FIG. 2 is that the products, alkyl oxy-esters (i.e., R—OY), generated from direct oxidation of an alkene, Eq 1, are a liquid product that is less reactive than the corresponding alkene. Separation and hydrolysis of the ester groups give the corresponding glycol and two equivalents of the oxy-acid (Eq. 2). Regeneration of the reduced electrophilic oxidant, M, with $O_2$ in the presence of the recycled oxy-acids, 2 HOY, completes the cycle (Eq. 3).

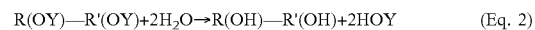

$$M+2HOY+\tfrac{1}{2}O_2 \to M(OY)_2 + H_2O \quad \text{(Eq. 3)}$$

$$R=R'+\tfrac{1}{2}O_2+H_2O \to R(OH)-R'(OH) \quad \text{(Net)}$$

The process comprises oxidizing an alkene. As used herein, the term "alkene" refers to any organic molecule comprising at least one olefinic moeity (i.e., two adjacent $sp^2$ hybridized carbon atoms with a double bond between them). For example, the alkene (i.e., alkene-containing compound) can be substituted or unsubstituted, and can be branched, straight-chained, cyclic, or include an aromatic ring, or a combination thereof, provided that the alkene has at least one olefinic bond (e.g., one olefinic bond, two olefinic bonds, three olefinic bonds, four olefinic bonds, or more). In some embodiments, the alkene is a $C_2$-$C_{20}$ alkene, a $C_2$-$C_{20}$ heteroalkene, $C_3$-$C_{20}$ cycloalkene, $C_3$-$C_{20}$ heterocycloalkene, arylalkene, heteroarylalkene, or a combination thereof. In further embodiments, the alkene is ethene, propene, or a mixture thereof.

The term "$C_2$-$C_{20}$ alkene" refers to a substituted or unsubstituted $C_2$-$C_{20}$ alkyl carbon chain from 2 to 20 (i.e., 2, 3, 4, 5, 6, 7, 8, 9, 10, 11, 12, 13, 14, 15, 16, 17, 18, 19, or 20) carbons in length comprising at least one olefinic moiety (i.e., two adjacent $sp^2$ hybridized carbon atoms with a double bond between them). In some embodiments, the $C_2$-$C_{20}$ alkene can be branched or straight-chained, so long as the $C_2$-$C_{20}$ alkene comprises at least one olefinic bond. An exemplary, but non-limiting list of $C_2$-$C_{20}$ alkenes includes ethylene, propylene, 1-butene, 2-butene, isobutylene, butadiene, 1-pentene, 2-pentene, isopentene, isoamylene, 2-methyl-1-butene, piperylene, and a combination thereof.

As used herein, "$C_2$-$C_{20}$ heteroalkene" refers to a substituted or unsubstituted $C_2$-$C_{20}$ alkene which contains at least 1 heteroatom (e.g., O, S, N, and/or P) in the core of the molecule (i.e., any part of the molecule except for the olefinic portion). Accordingly, at least 1 heteroatom can be a pendant substituent or part of a carbon chain. In certain instances, the $C_2$-$C_{20}$ heteroalkene has at least 2 heteroatoms in the core of the molecule, for example, at least 3, 4, 5, or 6 heteroatoms in the core of the molecule. In some embodiments, the $C_2$-$C_{20}$ heteroalkene compound comprises a moiety selected from an ether, an ester, a carbonate, an amide, an amine, a carbamate, a thioether, a thioester, a phosphate, a haloalkane, an acetyl, an alcohol, a ketone, an aldehyde, a carboxylate, a carboxylic acid, a hemiacetal, an acetal, a ketal, and imine, an imide, a thiol, a disulfide, a sulfoxide, and a thioketone, or any combination thereof. For example, the heteroalkene (i.e., heteroalkene-containing compound) can be substituted or unsubstituted, and can be branched, straight-chained, cyclic, or include an aromatic ring, or a combination thereof.

The term "$C_3$-$C_{20}$ cycloalkene," as used herein, refers to a substituted or unsubstituted $C_3$-$C_{20}$ alkene comprising a cyclic alkene moiety containing from, for example, 3 to 6 carbon atoms or from 5 to 6 carbon atoms. In some embodiments, the $C_3$-$C_{20}$ cycloalkene is cyclopropene, cyclobutene, cyclopentene, cyclohexene, norbornene, cyclopentadiene, or dicyclopentadiene.

The term "$C_3$-$C_{20}$ heterocycloalkene," as used herein, refers to a $C_3$-$C_{20}$ alkene comprising a cyclic alkene moiety containing from, for example, 3 to 6 carbon atoms or from 5 to 6 carbon atoms which contains at least 1 heteroatom (e.g., O, S, N, and/or P) in the core of the molecule (i.e., any part of the molecule except for the olefinic portion). Accordingly, at least 1 heteroatom can be a pendant substituent or part of a cyclic chain. In certain instances, the $C_3$-$C_{20}$ heterocycloalkene has at least 2 heteroatoms in the core of the molecule, for example, at least 3, 4, 5, or 6 heteroatoms in the core of the molecule. In some embodiments, the $C_3$-$C_{20}$ heterocycloalkene compound comprises a moiety selected from an ether, an ester, a carbonate, an amide, an amine, a carbamate, a thioether, a thioester, a phosphate, a haloalkane, an acetyl, an alcohol, a ketone, an aldehyde, a carboxylate, a carboxylic acid, a hemiacetal, an acetal, a ketal, an imine, and imide, a thiol, a disulfide, a sulfoxide, and a thioketone, or any combination thereof. An exemplary, but non-limiting list of $C_3$-$C_{20}$ heterocycloalkenes includes dihydrofuran, cyclohexenone, and 2-cyclohexenylethanol.

As used herein, "arylalkene" refers to a $C_6$-$C_{20}$ alkene comprising a substituted or unsubstituted, monocyclic or polycyclic aromatic substrate (e.g., phenyl, xylenyl, naphthyl, biphenyl, anthracyl, or a combination thereof). An exemplary arylalkene is styrene.

As used herein, "heteroarylalkene" refers to a $C_6$-$C_{20}$ arylalkene which contains at least 1 heteroatom (e.g., O, S, N, and/or P) in the core of the molecule (i.e., any part of the molecule except for the olefinic portion). Accordingly, at least 1 heteroatom can be a pendant substituent or part of a monocyclic or polycylic heteroaromatic core. In certain instances, the heteroarylalkene has at least 2 heteroatoms in the core of the molecule (e.g., at least 3, 4, 5, or 6 heteroatoms in the core of the molecule).

In some embodiments, the heteroarylalkene comprises a monocyclic or polycyclic heteroaromatic substrate. The term "heteroaromatic substrate" refers to an aromatic compound which has at least one heteroatom (O, S, or N) in at least one of the rings. In certain embodiments, the heteroaromatic substrate is polycyclic and has from 2 to 4 aromatic rings (i.e., 2, 3, or 4). Each ring of the heteroaromatic substrate containing a heteroatom can contain one or two oxygen and/or sulfur atoms and/or from one to four nitrogen atoms provided that the total number of heteroatoms in each ring is four or less and each ring has at least one carbon atom. The fused rings completing the polycyclic groups can contain only carbon atoms and can be saturated, partially saturated, or unsaturated. The nitrogen and sulfur atoms can optionally be oxidized, and the nitrogen atoms can optionally be quaternized. Heteroaromatic substrates that are polycyclic must include at least one fully aromatic ring but the other fused ring or rings can be aromatic or non-aromatic. In some embodiments, the heteroaromatic substrate is pyrrolyl, isoindolyl, indolizinyl, indolyl, furanyl, benzofuranyl, benzothiophenyl, thiophenyl, pyridyl, acridinyl, naphthyridinyl, quinolinyl, isoquinolinyl, isoxazolyl, oxazolyl, benzoxazolyl, isothiazolyl, thiazolyl, benzthiazolyl, imidazolyl, thiadiazolyl, tetrazolyl, triazolyl, oxadiazolyl, benzimidazolyl, purinyl, pyrazolyl, pyrazinyl, pteridinyl, quinoxalinyl, phthalazinyl, quinazolinyl, triazinyl, phenazinyl, cinnolinyl, pyrimidinyl, pyridazinyl, or a combination thereof.

As used herein, the term "substituted" can mean that one or more hydrogens on the designated atom or group are replaced with another group provided that the designated atom's normal valence is not exceeded. For example, when the substituent is oxo (i.e., =O), then two hydrogens on the atom are replaced. In certain embodiments, the substituent is halo (e.g., fluoro, chloro, bromo, iodo), hydroxyl, cyano, nitro, alkoxy, amino, aryl, heteroaryl, alkyl, heteroalkyl, oxo, or combinations thereof. Combinations of substituents and/or variables are permissible provided that the substitutions do not significantly adversely affect synthesis or use of the compound. The substituted moiety typically comprises at least one substituent (e.g., 1, 2, 3, 4, 5, 6, etc.) in any suitable position (e.g., 1-, 2-, 3-, 4-, 5-, or 6-position, etc.).

The oxygenate produced in step (a) can be any suitable oxidized intermediate. Generally, the oxidized intermediate is any compound formed through the process of an oxidation, an oxygenation, or a combination thereof. In certain embodiments, the oxygenate has undergone a displacement and/or dehydration with an oxygen acid to produce a modified product, such as an ester. In certain embodiments, the oxygenate has undergone a hydration reaction to produce a modified product, such as an alcohol, a diol, or a polyol comprising three or more hydroxyl groups. In certain instances, the oxidized intermediate is oxidized in at least one position, for example, the oxidized intermediate can be oxidized in two different positions or more (e.g., three or more, four or more, or five or more different positions). In some embodiments, the oxidized intermediate has been oxidized in two or more (e.g., 3 or more, 4 or more, or 5 or more) different positions with the same functional group or at least two different functional groups. In preferred embodiments, the oxygenate has been oxidized in two different positions with the same functional group. Typically, the oxygenate comprises one or more alcohol functionalities, one or more ester functionalities, or a combination thereof.

In some embodiments, the oxidized intermediate is an alkyl electrophile intermediate. As used herein, the term "alkyl electrophile intermediate" refers to an intermediate where the oxidizing electrophile has undergone an electrophilic addition reaction to produce a metal-carbon bond. Without wishing to be bound by any particular theory, it is believed that the alkyl electrophile intermediate can proceed to form an oxygenate.

The oxidizing electrophile or reduced form of the oxidizing electrophile comprises a main group element. The main group element typically includes elements in the post-transition metal and non-metal groups of the periodic table and include, for example, elements with atomic numbers 31, 32, 33, 34, 35, 49, 50, 51, 52, 53, 81, 82, and 83. In an embodiment, the term "main group element" typically refers to any element having filled 4d or 5d orbitals, which undergoes a net one- or two-electron change in oxidation state. Suitable main group elements include thallium, indium, lead, antimony, mercury, tin, selenium, tellurium, arsenic, cadmium, iodine, and bismuth. In some embodiments, the main group element is antimony, tellurium, bismuth, or arsenic. In some embodiments, the oxidizing electrophile comprises iodine. In further embodiments, the oxidizing electrophile comprises Sb(V), Te(VI), Te(IV), Bi(V), Se(VI), Se(IV), As(V), I(V), I(III), or Sn(IV).

The process comprises contacting the alkene with an oxidizing electrophile comprising a main group element in oxidized form. The main group element in oxidized form can be any suitable main group element in any suitable oxidation state. For example, the main group element can have an oxidation state of +7, +6, +5, +4, +3, +2, or +1, particularly an oxidation state of +6, +5, +4, +3, or +2. In preferred embodiments, the main group element in oxidized form has any oxidation state suitable for a one- or two-electron reduction/oxidation process.

In some embodiments, the process comprises contacting the alkene with an oxidant and a reduced form of an oxidizing electrophile. As used herein, "a reduced form of the oxidizing electrophile" refers to any reduced form of an oxidizing electrophile comprising a main group element. Generally, the reduced form of the oxidizing electrophile comprises a main group element with a one- or two-electron difference in oxidation state, relative to the oxidizing electrophile comprising a main group element in oxidized form. For example, the reduced form of the oxidizing electrophile will have a main group element in an oxidation state of +6, +5, +4, +3, +2, or +1, or a neutral oxidation state. In certain embodiments, the reduced form of the oxidizing electrophile comprises the main group element in an oxidation state of +4, +3, +2, or +1, or a neutral oxidation state. In some embodiments, the reduced form of the oxidizing electrophile can be any suitable chemical variant of the oxidizing electrophile, such that the main group element has been reduced by one or two electrons, preferably two electrons.

In embodiments where the process comprises contacting the alkene with an oxidant and a reduced form of an oxidizing electrophile, the oxidant can be any suitable oxidant capable of generating the main group element in oxidized form. For example, the oxidant (e.g., the oxidizing regeneration reagent) can be molecular oxygen, air, a peroxide, nitric oxide, nitrous oxide, nitric acid, sulfur trioxide, ozone, or a combination thereof. The oxidant can be used under an inert atmosphere or in combination with air. The peroxide can be, e.g., an organic peroxide, inorganic peroxide, hydrogen peroxide, or a combination thereof. In some embodiments, the oxidant can be an organic oxidant. For example, the oxidant can be a quinone or a nitroxide. In certain embodiments, the oxidant is a quinone, molecular oxygen, air, a peroxide, nitric oxide, nitrous oxide, nitric acid, a nitroxide, sulfur trioxide, ozone, or a combination thereof.

The oxidizing electrophile can comprise at least one (e.g., 1, 2, 3, 4, 5, or 6) conjugate anion of an oxygen acid. As used herein, "oxygen acid" refers to any organic acid or inorganic acid which contains hydrogen, oxygen, and at least one other element, in which the protic hydrogen is attached to oxygen. Generally, the conjugate anion of an oxygen acid is selected from sulfite, sulfate, hydrogen sulfate, thiosulfate, nitrite, nitrate, phosphate, phosphite, hydrogen phosphate, dihydrogen phosphate, carbonate, hydrogen carbonate, oxalate, cyanate, isocyanate, chromate, dichromate, permanganate, carboxylate, sulfonate, borate, and any combination thereof.

In some embodiments, the conjugate anion of an oxygen acid is an electron-deficient alkoxide, aryloxide, or a combination thereof. As used herein, the term "electron-deficient alkoxide" refers to any alkoxide with at least one electron withdrawing substituent as described here. For example, the electron-deficient alkoxide can be trifluoroethoxide. As used herein, the term "aryloxide" refers to any oxide with an aryl group as described herein. For example, the electron-deficient aryloxide can be phenoxide with electron-withdrawing groups on the ring.

In some embodiments, the conjugate anion of an oxygen acid is selected from a carboxylate, a sulfate, a sulfonate, a phosphate, a borate, and a combination thereof. Typically, the carboxylate can be an aliphatic carboxylate (e.g., acetate), an aromatic carboxylate or a fluorinated carboxylate (e.g., trifluoroacetate (TFA)). Similarly, the sulfonate can be an aliphatic sulfonate (e.g., methanesulfonate), an aromatic sulfonate, or a fluorinated sulfonate (e.g., trifluoromethanesulfonate). The conjugate anion of the oxygen acid can be an aliphatic carboxylate, heteroaliphatic carboxylate, aromatic carboxylate, heteroaromatic carboxylate, aliphatic sulfonate, heteroaliphatic sulfonate, aromatic sulfonate, heteroaromatic sulfonate, aliphatic phosphate, heteroaliphatic phosphate, aromatic phosphate, heteroaromatic phosphate, aliphatic borate, heteroaliphatic borate, aromatic borate, heteroaromatic borate, or a mixture thereof. In some embodiments, the conjugate anion of the oxygen acid is trifluoroacetate, acetate, alkylsulfonate, phosphate, nitrate, sulfate, trifluoromethanesulfate, or fluorosulfate.

As used herein, "aliphatic" refers to a substituted or unsubstituted $C_1$-$C_9$ alkyl substituent, in which, "$C_1$-$C_9$ alkyl" refers to an alkyl carbon chain from 1 to 9 (i.e., 1, 2, 3, 4, 5, 6, 7, 8, or 9) carbons in length. In some embodiments, $C_1$-$C_9$ alkyl can be saturated, unsaturated, branched, straight-chained, cyclic, or a combination thereof. An exemplary, but non-limiting list of $C_1$-$C_9$ alkyl aliphatics includes methyl, ethyl, n-propyl, iso-propyl, n-butyl, sec-butyl, tert-butyl, n-pentyl, sec-pentyl, neo-pentyl, hexyl, heptyl, octyl, nonyl, cyclopentyl, cyclohexyl, propenyl, 2-butenyl, 3-butenyl, 2-pentenyl, 3-pentenyl, 4-pentenyl, and a combination thereof. In certain embodiments, the aliphatic group is perfluorinated.

As used herein, "heteroaliphatic" refers to refers to a substituted or unsubstituted $C_1$-$C_9$ alkyl substituent which contains at least 1 heteroatom (e.g., O, S, N, and/or P) in the core of the molecule (i.e., the carbon backbone). The $C_1$-$C_9$ alkyl substituent can be saturated, unsaturated, branched, straight-chained, cyclic, or a combination thereof. In certain instances, the heteroaliphatic substituent has at least 2 heteroatoms in the core of the molecule (e.g., at least 3, 4, 5, or 6 heteroatoms in the core of the molecule). In some embodiments, the heteroaliphatic compound is an ether, an ester, a carbonate, an amide, an amine, a carbamate, a thioether, a thioester, a phosphate, a heterocycloalkane, or a combination thereof. In certain embodiments, the heteroaliphatic group is perfluorinated.

As used herein, "aromatic" refers to a substituted or unsubstituted, monocyclic or polycyclic aromatic substituent. The aromatic substituent can be any suitable aromatic substituent. An exemplary, but non-limiting list of aromatic substituents includes phenyl, xylenyl, naphthyl, biphenyl, anthracyl, or a combination thereof. In certain embodiments, the aromatic group is perfluorinated.

As used herein, "heteroaromatic" refers to a substituted or unsubstituted, monocyclic or polycylic aromatic compound which has at least one heteroatom (e.g., 0, S, or N) in at least one of the rings. In certain embodiments, the heteroaromatic substituent is polycyclic and has 2, 3, or 4 aromatic rings. Each ring of the heteroaromatic substituent containing a heteroatom can contain one or two oxygen and/or sulfur atoms and/or from one to four nitrogen atoms, provided that the total number of heteroatoms in each ring is 4 or less and each ring has at least one carbon atom. The fused rings completing the polycyclic groups can contain only carbon atoms and can be saturated, partially saturated, or unsaturated. The nitrogen and sulfur atoms can optionally be oxidized, and the nitrogen atoms can optionally be quaternized. Heteroaromatic substituents that are polycyclic must include at least one fully aromatic ring but the other fused ring(s) can be aromatic or non-aromatic. In some embodiments, the heteroaromatic substituent is pyrrolyl, isoindolyl, indolizinyl, indolyl, furanyl, benzofuranyl, benzothiophenyl, thiophenyl, pyridyl, acridinyl, naphthyridinyl, quinolinyl, isoquinolinyl, isoxazolyl, oxazolyl, benzoxazolyl, isothiazolyl, thiazolyl, benzthiazolyl, imidazolyl, thiadiazolyl, tetrazolyl, triazolyl, oxadiazolyl, benzimidazolyl, purinyl, pyrazolyl, pyrazinyl, pteridinyl, quinoxalinyl, phthalazinyl, quinazolinyl, triazinyl, phenazinyl, cinnolinyl, pyrimidinyl, pyridazinyl, or a combination thereof. In certain embodiments, the heteroaromatic group is perfluorinated.

In some embodiments, the oxidizing electrophile is of the formula $M^{+n}X_pL_q$, wherein M is a main group element cation in an oxidation state of n, X is the conjugate anion of an oxygen acid, L is a ligand, n is an integer from 2 to 6 (i.e., 2, 3, 4, 5, or 6), p is an integer from 1 to 6 (i.e., 1, 2, 3, 4, 5, or 6), and q is an integer from 0 to 5 (i.e., 0, 1, 2, 3, 4, or 5). The oxidizing electrophile of the formula $M^{+n}X_pL_q$ can have any suitable net charge, such as +5, +4, +3, +2, or +1, or a neutral net charge. In certain embodiments, the oxidizing electrophile of the formula $M^{+n}X_pL_q$ is a neutral species. Without wishing to be bound to any particular theory, the reactive species $[M^{+n}X_p]$ can have up to q number of ligands (L) to either balance the net charge of $[M^{+n}X_p]$ and/or solvate the remaining charge of $[M^{+n}X_p]$. In some embodiments, $M^{+n}X_pL_q$ undergoes reaction with the alkene in the liquid medium to yield a reduced form of the oxidizing electrophile of formula $M^{+(n-2)}X_{p-2}L_q$ or $M^{+(n-1)}X_{p-1}L_q$.

In certain embodiments, the reduced form of the oxidizing electrophile is of the formula $M^{+n-2}X_{p-2}L_q$ or $M^{+n-1}X_{p-1}L_q$, wherein M, X, L, n, p, and q are as described herein. In certain embodiments, n and p are the same or different and each is an integer from 2 to 6 (i.e., 2, 3, 4, 5, 6), and q is an integer from 0 to 4 (i.e., 0, 1, 2, 3, or 4).

X of any of the foregoing formulas can be any suitable conjugate anion of an oxygen acid, as described herein, in any suitable oxidation state. Generally, X is one or more selected from an aliphatic carboxylate, heteroaliphatic carboxylate, aromatic carboxylate, heteroaromatic carboxylate, aliphatic sulfonate, heteroaliphatic sulfonate, aromatic sulfonate, heteroaromatic sulfonate, aliphatic phosphate, heteroaliphatic phosphate, aromatic phosphate, heteroaromatic phosphate, aliphatic borate, heteroaliphatic borate, aromatic borate, and heteroaromatic borate. As used herein, carboxylates can be alkylated variants (e.g., acetate), fluorinated variants (e.g., trifluoroacetate (TFA)), or arylated variants (e.g., benzoates or benzoic acids). As used herein, "alkylated variants" and "arylated variants" refer to a carboxylic acid containing an alkyl group or an aryl group, respectively, as defined herein. Similarly, sulfonates can be alkylated variants (e.g., methanesulfonate) or fluorinated variants (e.g., trifluoromethanesulfonate). In certain embodiments, X is one or more selected from trifluoroacetate, acetate, benzoate, sulfate, methanesulfonate, and trifluoromethanesulfonate. Typically, X has an oxidation state of −4, −3, −2, or −1.

The ligand (L) can be any ligand that suitably coordinates to the main group element (M). Generally, each ligand is the same or different and each can be anionic or neutral. In some embodiments, each ligand (L) is independently an oxide (e.g., a bridging oxide (bridging oxo) or a terminal oxide (terminal oxo)), hydroxide, or combination thereof. In certain embodiments, the ligand is anionic and helps balance the charge of the oxidizing electrophile. In certain embodiments, the ligand is neutral and helps solvate the charge of the oxidizing electrophile. In some embodiments, the ligand is the non-oxidizable liquid (e.g., solvent), an alkene molecule, a product of the alkene oxidation, or a combination thereof.

In some embodiments, the ligand is at least one monodentate or bidentate ligand that is aliphatic-based or aromatic-based and comprises at least one oxo, thiol, sulfonyl, or carboxyl group, and optionally comprises one or more electron withdrawing groups. In certain embodiments, the ligand comprises at least one carboxyl group. As used herein, "aliphatic-based" or "aromatic-based" refer to the ligand as a whole, and the ligand can be bound directly to the aliphatic or aromatic portion, or indirectly via at least one oxo, thiol, sulfonyl, or carboxyl group. The terms "aliphatic" and "aromatic" are as described herein.

In certain embodiments, the ligand is aromatic-based. In embodiments where the ligand is aromatic-based, the ligand can comprise at least one carboxyl group and at least one nitro group.

In certain embodiments, the ligand is selected from the group consisting of:

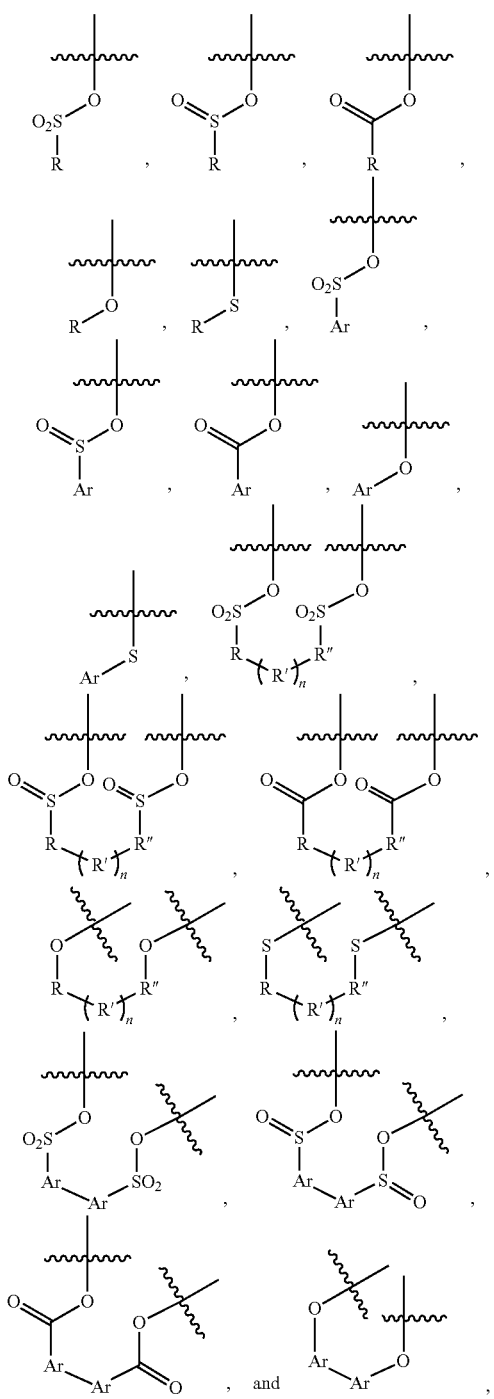

wherein R, R', and R" are the same or different and each is an optionally substituted alkyl, Ar is an optionally substituted aryl, EWG is at least one electron withdrawing group, and n is 0 or an integer of 1 to 6.

The ligand also can be of the formula —Ar-EWG, wherein Ar is an optionally substituted aryl and EWG is at least one electron withdrawing group, as described herein. For example, the electron withdrawing group can be at least one moiety selected from —$NO_2$, fluoro-$C_{1-8}$ alkyl, —F, —OOCR, —COOH, —$OH_2^+$, —$CONH_2$, —COOR, —$NR_3^+$, —CN, —$SO_3H$, —$SO_3R$, —$SO_3W$, and a combination thereof. In the context of the electron withdrawing group, R is hydrogen or any optionally substituted aliphatic (e.g., $C_{1-8}$ alkyl, fluoro-$C_{1-8}$ alkyl), heteroaliphatic, aromatic, or heteroaromatic, and W is a cation comprising a metal selected from boron, bismuth, antimony, arsenic, lanthanum, cerium, scandium, yttrium, titanium, zirconium, hafnium, silver, zinc, cadmium, aluminum, gallium, indium, germanium, tin, phosphorus, an alkali metal, or an alkaline earth metal.

For example, the ligand can be:

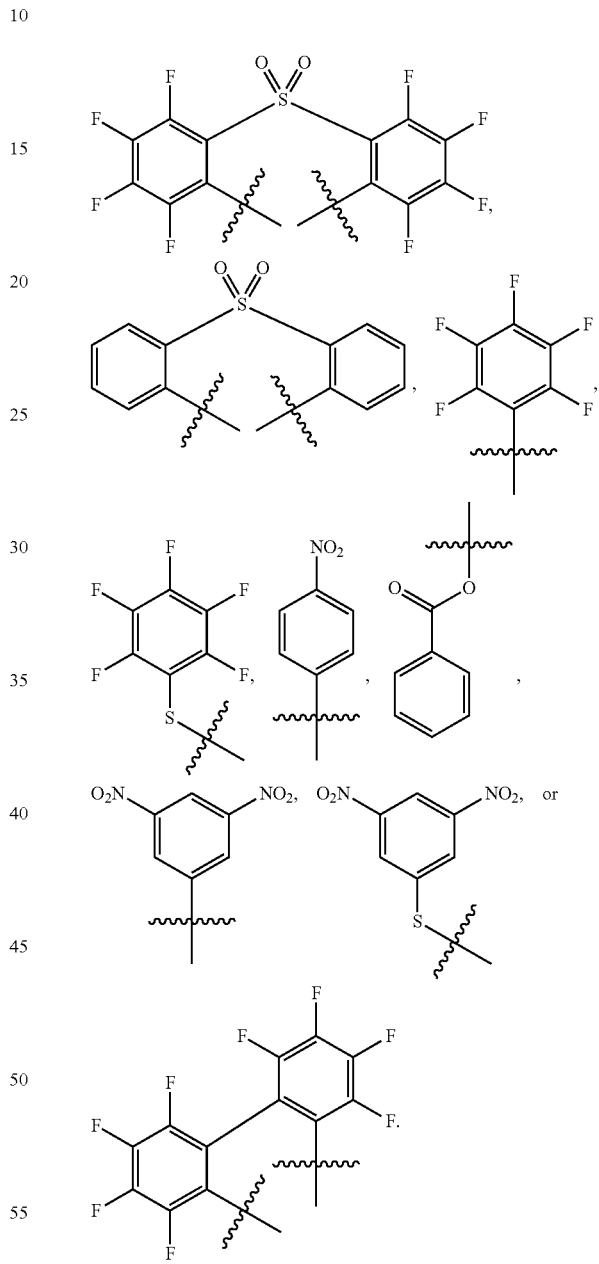

The ligand can be present in the mixture in less than stoichiometric quantities relative to the main group element, stoichiometric quantities relative to the main group element, or at least stoichiometric quantities relative to the main group element.

Figure 3:
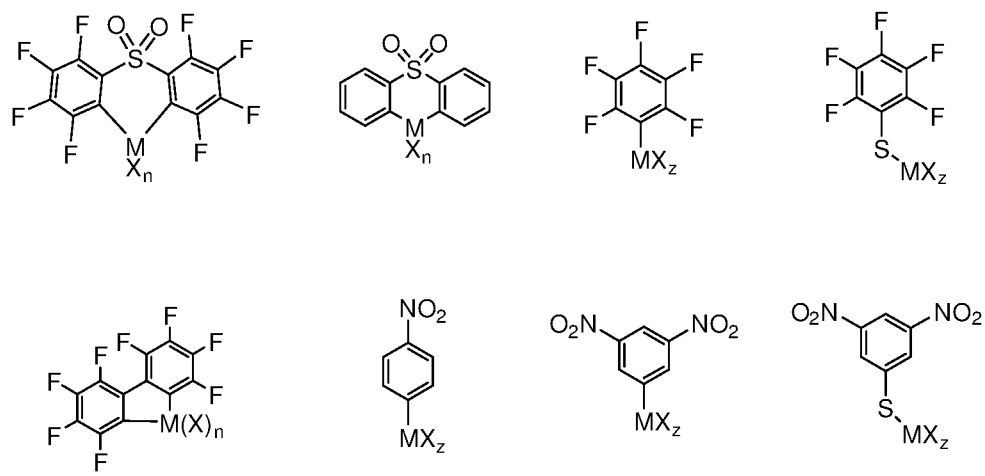
FIG. 3 is a list of exemplary oxidizing electrophiles.

In some embodiments, the oxidizing electrophile has a formula according to any one of the structures in FIG. 3.

The oxidizing electrophile can be prepared using any suitable method. For example, the oxidizing electrophile can be prepared separately as a stable and isolable compound or the oxidizing electrophile can be generated in situ from a reduced form of the oxidizing electrophile, generated in situ through a substitution reaction, or generated in situ through a dehydration reaction. A combination of any of these methods can also be used.

In some embodiments, the oxidizing electrophile comprising a main group element is present in at least stoichiometric quantities relative to the amount of oxygenate produced (i.e., relative to the amount of alkene that reacts with the oxidizing electrophile). Typically, when the oxidizing electrophile is present in at least a stoichiometric quantity relative to the oxygenate, an oxidizing regeneration reagent is not present in the reaction. In other embodiments, the oxidizing electrophile is present in a sub-stoichiometric quantity relative to the oxygenate. Typically, when the oxidizing electrophile is present in a sub-stoichiometric quantity, an oxidizing regeneration reagent and optionally an oxidative regeneration catalyst are present to regenerate the oxidizing electrophile from the reduced form of the oxidizing electrophile. In some preferred embodiments, the oxidizing electrophile is present in at least a stoichiometric quantity relative to the oxygenate and an oxidizing regeneration reagent and optionally an oxidative regeneration catalyst are not required, but can be present in the liquid medium. In other preferred embodiments, the oxidizing electrophile is present in a sub-stoichiometric quantity relative to the oxygenate and an oxidizing regeneration reagent or an oxidative regeneration catalyst are present. In some embodiments, the oxidizing electrophile comprising a main group element in oxidized form is present in less than stoichiometric quantities relative to the oxygenate and acts as a catalyst.

In some embodiments, the reduced form of the oxidizing electrophile can be present in at least stoichiometric quantities or a sub-stoichiometric quantity relative to the oxygenate (i.e., relative to the amount of alkene that reacts with the oxidizing electrophile). In some embodiments, the reduced form of the oxidizing electrophile is generated in situ from the reduction of the oxidizing electrophile upon formation of the oxygenate. In these instances, the reduced form of the oxidizing electrophile is used to regenerate the oxidizing electrophile. In other embodiments, the reduced form of the oxidizing electrophile is provided directly to the process for converting an alkene to an oxygenate. In these instances, the reduced form of the oxidizing electrophile is used to generate the oxidizing electrophile. Accordingly, when the reduced form of the oxidizing electrophile is provided directly to the process in at least stoichiometric quantities or sub-stoichiometric quantities, the oxidant is present in the reaction mixture to generate the oxidizing electrophile.

Thus, the process for oxidizing an alkene can comprise the oxidizing electrophile, the reduced form of the oxidizing electrophile, or both the oxidizing electrophile and the reduced form of the oxidizing electrophile. The amount of the oxidizing electrophile and/or the reduced form of the oxidizing electrophile is not particularly limited such that a sufficient amount of the oxidizing electrophile exists to oxidize the alkene. Accordingly, the oxidizing electrophile and/or the reduced form of the oxidizing electrophile can be present in an amount of about 0.1 mol % of the alkene or more (e.g., about 0.2 mol % or more, about 0.3 mol % or more, about 0.4 mol % or more, about 0.5 mol % or more, about 1 mol % or more, about 2 mol % or more, about 3 mol % or more, about 5 mol % or more, about 10 mol % or more, about 20 mol % or more, about 50 mol % or more, or about 100 mol % or more). Alternatively, or in addition, the oxidizing electrophile and/or the reduced form of the oxidizing electrophile can be present in an amount of about 2000 mol % of the alkene or less (e.g., about 1500 mol % or less, about 1000 mol % or less, about 900 mol % or less, about 800 mol % or less, about 700 mol % or less, about 600 mol % or less, about 500 mol % or less, about 400 mol % or less, about 300 mol % or less, about 200 mol % or less, or about 100 mol % or less). Any two of the foregoing endpoints can be used to define a close-ended range, or any single endpoint can be used alone to define an open-ended range. For example, the oxidizing electrophile and/or the reduced form of the oxidizing electrophile can be present in an amount between about 0.1 mol % to about 2000 mol % of the alkene, for example, about 0.1 mol % to about 1500 mol %, about 0.1 mol % to about 1000 mol %, about 0.1 mol % to about 900 mol %, about 0.1 mol % to about 800 mol %, about 0.1 mol % to about 700 mol %, about 0.1 mol % to about 600 mol %, about 0.1 mol % to about 500 mol %, about 0.1 mol % to about 400 mol %, about 0.1 mol % to about 300 mol %, about 0.1 mol % to about 200 mol %, about 0.1 mol % to about 100 mol %, about 0.2 mol % to about 100 mol %, about 0.3 mol % to about 100 mol %, about 0.4 mol % to about 100 mol %, about 0.5 mol % to about 100 mol %, about 1 mol % to about 100 mol %, about 2 mol % to about 100 mol %, about 3 mol % to about 100 mol %, about 5 mol % to about 100 mol %, about 10 mol % to about 100 mol %, about 20 mol % to about 100 mol %, about 50 mol % to about 100 mol %, about 100 mol % to about 1000 mol %, or about 100 mol % to about 600 mol %.

In some embodiments, the liquid medium comprises an oxygen acid, such as aliphatic carboxylic acid, heteroaliphatic carboxylic acid, aromatic carboxylic acid, heteroaromatic carboxylic acid, aliphatic sulfonic acid, heteroaliphatic sulfonic acid, aromatic sulfonic acid, heteroaromatic sulfonic acid, aliphatic phosphonic acid, heteroaliphatic phosphonic acid, aromatic phosphonic acid, heteroaromatic phosphonic acid, boric acid, aliphatic boronic acid, heteroaliphatic boronic acid, aromatic boronic acid, heteroaromatic boronic acid, or a mixture thereof. Preferably, the oxygen acid is trifluoroacetic acid, acetic acid, methanesulfonic acid, phosphoric acid, nitric acid, sulfuric acid, trifluoromethanesulfonic acid, fluorosulfuric acid, or a mixture thereof.

In some embodiments, the oxygen acid is an electron-deficient alcohol, an aryl alcohol, or a combination thereof. As used herein, the term "electron-deficient alcohol" refers to any alcohol with at least one electron withdrawing substituent, as described herein. For example, the electron-deficient alcohol can be trifluoroethanol. As used herein, the term "aryl alcohol" refers to any alcohol with an aryl group, as described herein. For example, the aryl alcohol can be phenol.

In further embodiments, all or a portion of the oxygen acid is added as an anhydride of the oxygen acid. In preferred embodiments, a portion of the oxygen acid is added as an anhydride. Without wishing to be bound by any particular theory, it is believed that the anhydride can act as a water scavenger, resulting in a reduced amount of water in the liquid medium and in turn generating two molecules of the oxygen acid for every one molecule of water and anhydride.

The oxygen acid can be present in an amount of about 0.1 mol % of the oxidizing electrophile or more (e.g., about 0.2 mol % or more, about 0.3 mol % or more, about 0.4 mol % or more, about 0.5 mol % or more, about 1 mol % or more, about 2 mol % or more, about 3 mol % or more, about 5 mol % or more, about 10 mol % or more, about 20 mol % or more, about 50 mol % or more, or about 100 mol % or more). Alternatively, or in addition, the oxygen acid can be present in an amount of about 2000 mol % of the oxidizing electrophile or less (e.g., about 1500 mol % or less, about 1000 mol % or less, about 900 mol % or less, about 800 mol % or less, about 700 mol % or less, about 600 mol % or less, about 500 mol % or less, about 400 mol % or less, about 300 mol % or less, about 200 mol % or less, or about 100 mol % or less). Any two of the foregoing endpoints can be used to define a close-ended range, or can be used alone to define an open-ended range. Thus, the oxygen acid can be present in an amount between about 0.1 mol % to about 2000 mol % of the oxidizing electrophile, for example, about 0.1 mol % to about 1500 mol %, about 0.1 mol % to about 1000 mol %, about 0.1 mol % to about 900 mol %, about 0.1 mol % to about 800 mol %, about 0.1 mol % to about 700 mol %, about 0.1 mol % to about 600 mol %, about 0.1 mol % to about 500 mol %, about 0.1 mol % to about 400 mol %, about 0.1 mol % to about 300 mol %, about 0.1 mol % to about 200 mol %, about 0.1 mol % to about 100 mol %, about 0.2 mol % to about 100 mol %, about 0.3 mol % to about 100 mol %, about 0.4 mol % to about 100 mol %, about 0.5 mol % to about 100 mol %, about 1 mol % to about 100 mol %, about 2 mol % to about 100 mol %, about 3 mol % to about 100 mol %, about 5 mol % to about 100 mol %, about 10 mol % to about 100 mol %, about 20 mol % to about 100 mol %, about 50 mol % to about 100 mol %, about 100 mol % to about 1000 mol %, or about 100 mol % to about 600 mol %.

Depending on the embodiment, the liquid medium comprises one or more additives, such as a non-oxidizable liquid, a salt additive, a Lewis acid, and water. Desirably, the additives can be used to provide a functional benefit to the reaction mixture (e.g., liquid medium), such as solvation, solubilization, viscosity modification, and/or charge transfer.

The amount of additive is not particularly limited such that the additive can be used in amounts that are a fraction of the amount of oxidizing electrophile or in amounts that are in a large excess of the amount of oxidizing electrophile. The one or more additives can be present in an amount of about 0.1 mol % of the oxidizing electrophile or more (e.g., about 0.2 mol % or more, about 0.3 mol % or more, about 0.4 mol % or more, about 0.5 mol % or more, about 1 mol % or more, about 2 mol % or more, about 3 mol % or more, about 5 mol % or more, about 10 mol % or more, about 20 mol % or more, about 50 mol % or more, or about 100 mol % or more). Alternatively, or in addition, the one or more additives can be present in an amount of about 2000 mol % of the oxidizing electrophile or less (e.g., about 1500 mol % or less, about 1000 mol % or less, about 900 mol % or less, about 800 mol % or less, about 700 mol % or less, about 600 mol % or less, about 500 mol % or less, about 400 mol % or less, about 300 mol % or less, about 200 mol % or less, or about 100 mol % or less). Any two of the foregoing endpoints can be used to define a close-ended range, or any single endpoint can be used alone to define an open-ended range. Thus, the one or more additives can be present in an amount between about 0 mol % to about 2000 mol % of the oxidizing electrophile, for example, about 0 mol % to about 1500 mol %, about 0 mol % to about 1000 mol %, about 0 mol % to about 900 mol %, about 0 mol % to about 800 mol %, about 0 mol % to about 700 mol %, about 0 mol % to about 600 mol %, about 0 mol % to about 500 mol %, about 0 mol % to about 400 mol %, about 0 mol % to about 300 mol %, about 0 mol % to about 200 mol %, about 0 mol % to about 100 mol %, about 0.1 mol % to about 100 mol %, about 0.2 mol % to about 100 mol %, about 0.3 mol % to about 100 mol %, about 0.4 mol % to about 100 mol %, about 0.5 mol % to about 100 mol %, about 1 mol % to about 100 mol %, about 2 mol % to about 100 mol %, about 3 mol % to about 100 mol %, about 5 mol % to about 100 mol %, about 10 mol % to about 100 mol %, about 20 mol % to about 100 mol %, about 50 mol % to about 100 mol %, about 100 mol % to about 1000 mol %, or about 100 mol % to about 600 mol %. In some embodiments, the additive is not present in the liquid medium. Thus, the additive can be present in an amount of 0 mol % of the oxidizing electrophile.

In some embodiments, the liquid medium comprises at least one non-oxidizable liquid. The non-oxidizable liquid can be any suitable liquid (e.g., fluid or solvent) such that the liquid does not interfere with the process for oxidizing an alkene. In some embodiments, the oxygenate is the non-oxidizable liquid (e.g., fluid or solvent). In certain embodiments, the liquid can be considered substantially inert under the reaction conditions. In some embodiments, the liquid is substantially inert in the presence of the oxidizing electrophile.

As used herein, "substantially inert" refers to a liquid (e.g., fluid or solvent) that maintains greater than about 80% stability in the presence of the oxidizing electrophile, such as measured by the retention of the non-oxidizable liquid peaks in a $^1$H Nuclear Magnetic Resonance (NMR) spectrum, relative to a standard. In certain embodiments, the liquid can maintain greater than about 85% stability in the presence of the oxidizing electrophile, for example, greater than about 90% stability in the presence of the oxidizing electrophile, greater than about 92% stability in the presence of the oxidizing electrophile, greater than about 94% stability in the presence of the oxidizing electrophile, greater than about 95% stability in the presence of the oxidizing electrophile, greater than about 98% stability in the presence of the oxidizing electrophile, or greater than about 99% stability in the presence of the oxidizing electrophile. Ideally, the liquid is totally inert to the oxidizing conditions but with strong oxidants it can be expected that a small amount of liquid may be consumed or lost in subsequent recycle steps.

As used herein, the terms "liquid" or "liquid medium" refer to any medium that comprises a liquid. For example, the liquid or liquid medium can exist as a liquid-solid medium, a liquid-gas medium, a liquid-liquid medium, a liquid-gas-solid medium, etc. Accordingly, the liquid or liquid medium can be, for example, a solution, a gas-sparged liquid, a gel, a colloid, a slurry, a dispersion, an emulsion, or a combination thereof.

In some embodiments, the non-oxidizable liquid is selected from a fluorinated hydrocarbon, a sulfone, a deactivated arene, a deactivated aliphatic, a deactivated heteroarene, a deactivated heteroaliphatic, a carbonate, and a combination thereof.

In some embodiments, the non-oxidizable liquid is one or more suitable fluorinated hydrocarbon(s). The fluorinated hydrocarbon can be at least one fluorinated or perfluorinated straight chain aliphatic comprising at least 2 carbons, for example, at least 3, 4, 5, 6, 7, 8, 9, 10, 11, 12, 13, 14, 15, or 16 carbons. Preferably, the fluorinated hydrocarbon is at least one fluorinated or perfluorinated cyclic aliphatic comprising at least 3 carbons, for example, at least 4, 5, 6, 7, 8, 9, or 10 carbons. In some embodiments, the fluorinated or perfluorinated cyclic aliphatic can be monocyclic, bicyclic, or tricyclic. The fluorinated hydrocarbon can be perfluorinated and is branched or straight, and either substituted or unsubstituted. Preferably, the fluorinated or perfluorinated straight chain aliphatic and/or the fluorinated or perfluorinated cyclic aliphatic is substituted with one or more aliphatic substituents. More preferably, the fluorinated hydrocarbon is perfluorinated.

Specific examples include perfluroropentane, perfluorohexane, perfluoroheptane, perfluorooctane, perfluorononane, perfluorodecane, perfluorocyclohexane, perfluorocycloheptane, perfluorocyclooctane, perfluorodecalin, perfluoromethylcyclohexane, perfluorodimethylcyclohexane, perfluorotrimethylcyclohexane, perfluoroethylcyclohexane, perfluorodiethylcyclohexane, perfluorotriethylcyclohexane, perfluoroethylmethylcyclohexane, and perfluoro-2,2,3,3-tetramethylbutane.

In some embodiments, the non-oxidizable liquid is one or more sulfone(s) of the formula:

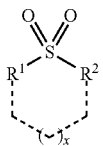

in which $R^1$ and $R^2$ are independently chosen from an aryl group and alkyl group, each of which is optionally substituted, the dashed lines represent optional bonds and atoms (e.g., C, N, O, S, or P), and x is an integer from 0 to 3 (i.e., 0, 1, 2, or 3). In certain embodiments, $R^1$ and $R^2$ are connected by a chain to produce a cyclic sulfone.

In some embodiments, the sulfone is at least one alkyl sulfone, in which both $R^1$ and $R^2$ are independently chosen as alkyl groups. The alkyl group can be any suitable straight chain, branched, or cyclic alkyl group (e.g., $C_{1-9}$ alkyl). In certain embodiments, the alkyl group is substituted with at least 1 electron withdrawing substituent (e.g., at least 2, 3, or 4 electron withdrawing substituents), such as those described herein. In certain embodiments, the alkyl groups are connected by an alkylene chain to produce a cyclic alkyl sulfone, such as sulfolane.

As used herein, "alkyl" refers to an aliphatic substituent that can be substituted, unsubstituted, branched, straight-chained, cyclic, or a combination thereof, and can be fully saturated or include portions that are unsaturated or aromatic. In some embodiments, the alkyl is $C_1$-$C_9$ alkyl, such as methyl, ethyl, n-propyl, iso-propyl, n-butyl, sec-butyl, tert-butyl, n-pentyl, sec-pentyl, neo-pentyl, hexyl, heptyl, octyl, nonyl, cyclopentyl, cyclohexyl, propenyl, 2-butenyl, 3-butenyl, 2-pentenyl, 3-pentenyl, 4-pentenyl, or a combination thereof.

In some embodiments, the alkyl is a heteroalkyl group, a cycloalkyl group, or a heterocycloalkyl group.

As used herein, "heteroalkyl" refers to a substituted or unsubstituted alkyl which contains at least 1 heteroatom (e.g., O, S, N, and/or P) in the core of the molecule (i.e., any part of the molecule except for the alkane-containing portion). Accordingly, at least 1 heteroatom can be a pendant substituent or part of a carbon chain. In certain instances, the heteroalkyl group has at least 2 heteroatoms in the core of the molecule (e.g., at least 3, 4, 5, or 6 heteroatoms in the core of the molecule). In some embodiments, the heteroalkyl group comprises a moiety selected from an ether, an ester, a carbonate, an amide, an amine, a carbamate, a thioether, a phosphate, a heterocycloalkane, a haloalkane, an acetyl, an alcohol, a ketone, an aldehyde, a carboxylate, a carboxylic acid, a hemiacetal, an acetal, a ketal, an imine, and imide, a thiol, a disulfide, a sulfoxide, a thioketone, or a combination thereof.

The term "cycloalkyl," as used herein, refers to a substituted or unsubstituted alkyl group comprising a cyclic alkane moiety containing from, for example, 3 to 6 carbon atoms or from 5 to 6 carbon atoms. In some embodiments, the cycloalkyl group is cyclopropyl, cyclobutyl, cyclopentyl, or cyclohexyl. In some embodiments, the cycloalkyl can be a cycloalkenyl, as long as the cycloalkenyl comprises an alkane-containing portion. The term "cycloalkenyl" refers to a cycloalkane, as described herein, with at least one C—C double bond in the ring. For example, the cycloalkenyl can be cyclopentenyl or cyclohexenyl.

The term "heterocycloalkyl," as used herein, refers to an alkyl group comprising a cyclic alkane moiety containing from, for example, 3 to 6 carbon atoms or from 5 to 6 carbon atoms which contains at least 1 heteroatom (e.g., O, S, N, and/or P) in the core of the molecule (i.e., any part of the molecule except for the alkane-containing portion). Accordingly, at least 1 heteroatom can be a pendant substituent or encompassed in a cyclic chain. In certain instances, the heterocycloalkyl has at least 2 heteroatoms in the core of the molecule (e.g., at least 3, 4, 5, or 6 heteroatoms in the core of the molecule). In some embodiments, the heterocycloalkyl group comprises a moiety selected from an ether, an ester, a carbonate, an amide, an amine, a carbamate, a thioether, a thioester, a phosphate, a haloalkane, an acetyl, an alcohol, a ketone, an aldehyde, a carboxylate, a carboxylic acid, a hemiacetal, an acetal, a ketal, an imine, and imide, a thiol, a disulfide, a sulfoxide, a thioketone, or a combination thereof. An exemplary, but non-limiting list of heterocycloalkyl groups includes tetrahydrofuranyl, piperazinyl, morpholinyl, cyclohexanonyl, and 2-cyclohexylethanolyl.

As used herein, "aryl group" refers to any suitable substituted or unsubstituted aromatic or heteroaromatic group, as described herein. In some embodiments of the non-oxidizable liquid, the aryl group is deactivated, which means the aryl group is substituted with at least 1 electron withdrawing substituent, for example, at least 2, 3, or 4 electron withdrawing substituents, such as those described herein.

In some embodiments, the sulfone is a non-oxidizable liquid that contains a sulfonyl (—$SO_2$) functional group, such as (methylsulfonyl)benzene, (ethylsulfonyl)benzene, (propylsulfonyl)benzene, (isopropylsulfonyl)benzene, (butylsulfonyl)benzene, (methylsulfonyl)pyridine, (ethylsulfonyl)pyridine, (propylsulfonyl)pyridne, (isopropylsulfonyl)pyridine, (butylsulfonyl)pyridine, (cyclohexylsulfonyl)benzene, sulfonyldibenzene, dibenzothiophene 5,5-dioxide, 2,3-dihydrobenzothiophene 1,1-dioxide, or thiochromane 1,1-dioxide, each of which is substituted or unsubstituted.

In some embodiments, the sulfone is (methylsulfonyl)methane ("dimethyl sulfone"), (methylsulfonyl)ethane, tetrahydrothiophene 1,1-dioxide ("sulfolane"), tetrahydro-2H-thiopyran 1,1-dioxide, thietane 1,1-dioxide, (ethylsulfonyl)ethane, 1-(ethylsulfonyl)propane, 1-(propylsulfonyl)propane, 1-(propylsulfonyl)butane, 1-(butylsulfonyl)butane, 2-(ethylsulfonyl)propane, 2-(isopropylsulfonyl)propane, 1-(ethylsulfonyl)-2-methylpropane, 1-(methylsulfonyl)butane, 1-(ethylsulfonyl)butane, 1-(isopropylsulfonyl)-2-methylpropane, 1-(ethylsulfonyl)-2-methylpropane, 2-methyl-1-(methylsulfonyl)propane, 1-(isobutylsulfonyl)-2-methylpropane, 2-(tert-butylsulfonyl)-2-methylpropane, perfluorinated (methylsulfonyl)methane, perfluorinated (methylsulfonyl)ethane, perfluorinated tetrahydrothiophene 1,1-dioxide, perfluorinated tetrahydro-2H-thiopyran 1,1-dioxide, perfluorinated thietane 1,1-dioxide, perfluorinated (ethylsulfonyl)ethane, perfluorinated 1-(ethylsulfonyl)propane, perfluorinated 1-(propylsulfonyl)propane, perfluorinated 1-(propylsulfonyl)butane, perfluorinated 1-(butylsulfonyl)butane, perfluorinated 2-(ethylsulfonyl)propane, perfluorinated 2-(isopropylsulfonyl)propane, perfluorinated 1-(ethylsulfonyl)-2-methylpropane, perfluorinated 1-(methylsulfonyl)butane, perfluorinated 1-(ethylsulfonyl)butane, perfluorinated 1-(isopropylsulfonyl)-2-methylpropane, perfluorinated 1-(ethylsulfonyl)-2-methylpropane, perfluorinated 2-methyl-1-(methylsulfonyl)propane, perfluorinated 1-(isobutylsulfonyl)-2-methylpropane, or perfluorinated 2-(tert-butylsulfonyl)-2-methylpropane, each of which is substituted or unsubstituted.

In other embodiments, the sulfone is (methylsulfonyl)methane ("dimethyl sulfone"), (methylsulfonyl)ethane, tetrahydrothiophene 1,1-dioxide ("sulfolane"), tetrahydro-2H-thiopyran 1,1-dioxide, thietane 1,1-dioxide, perfluorinated (methylsulfonyl)methane, perfluorinated (methylsulfonyl)ethane, perfluorinated tetrahydrothiophene 1,1-dioxide, perfluorinated tetrahydro-2H-thiopyran 1,1-dioxide, or perfluorinated thietane 1,1-dioxide.

In some embodiments, the non-oxidizable liquid is one or more deactivated arene(s). As used herein, "deactivated arene" refers to at least one monocyclic or polycyclic aromatic compound that has 1 or more electron withdrawing substituents. In some embodiments, the arene compound has 2 or more electron withdrawing substituents, for example, 3 or more, 4 or more, 5 or more, or 6 or more electron withdrawing substituents. In some embodiments, each carbon of the deactivated arene has at least one electron withdrawing substituent. In certain embodiments, the deactivated arene is polycyclic and has 2, 3, or 4 aromatic rings and includes, e.g., benzene, toluene, xylene, naphthalene, biphenyl, and anthracene. The electron withdrawing substituent can be any suitable electron withdrawing substituent, such as those described herein.

An exemplary, but non-limiting list of deactivated arenes (e.g., deactivated benzenes) includes $C_6H_5(NO_2)$, $C_6H_5(CF_3)$, $C_6H_5F$, $C_6H_5(COOH)$, $C_6H_5(CONH_2)$, $C_6H_5(COOCF_3)$, $C_6H_5(OOCCF_3)$, $C_6H_5(CN)$, $C_6H_5(SO_3H)$, $C_6H_5(SO_3R)$, $C_6H_5(SO_3Q)$, m-$C_6H_4(NO_2)_2$, o-$C_6H_4(NO_2)_2$, p-$C_6H_4(NO_2)_2$, m-$C_6H_4(CF_3)_2$, o-$C_6H_4(CF_3)_2$, p-$C_6H_4(CF_3)_2$, m-$C_6H_4F_2$, o-$C_6H_4F_2$, p-$C_6H_4F_2$, m-$C_6H_4(COOH)_2$, o-$C_6H_4(COOH)_2$, p-$C_6H_4(COOH)_2$, m-$C_6H_4(CONH_2)_2$, o-$C_6H_4(CONH_2)_2$, p-$C_6H_4(CONH_2)_2$, m-$C_6H_4(COOCF_3)_2$, o-$C_6H_4(COOCF_3)_2$, p-$C_6H_4(COOCF_3)_2$, m-$C_6H_4(OOCCF_3)_2$, o-$C_6H_4(OOCCF_3)_2$, p-$C_6H_4(OOCCF_3)_2$, m-$C_6H_4(CN)_2$, o-$C_6H_4(CN)_2$, p-$C_6H_4(CN)_2$, m-$C_6H_4(SO_3H)_2$, o-$C_6H_4(SO_3H)_2$, p-$C_6H_4(SO_3H)_2$, m-$C_6H_4(SO_3R)_2$, o-$C_6H_4(SO_3R)_2$, p-$C_6H_4(SO_3R)_2$, m-$C_6H_4(SO_3Q)_2$, o-$C_6H_4(SO_3Q)_2$, p-$C_6H_4(SO_3Q)_2$, m-$C_6H_4(CF_3)(NO_2)$, o-$C_6H_4(CF_3)(NO_2)$, p-$C_6H_4(CF_3)(NO_2)$, m-$C_6H_4(CF_3)(F)$, o-$C_6H_4(CF_3)(F)$, p-$C_6H_4(CF_3)(F)$, m-$C_6H_4(CF_3)(COOH)$, o-$C_6H_4(CF_3)(COOH)$, p-$C_6H_4(CF_3)(COOH)$, m-$C_6H_4(CF_3)(CONH_2)$, o-$C_6H_4(CF_3)(CONH_2)$, p-$C_6H_4(CF_3)(CONH_2)$, m-$C_6H_4(CF_3)(CN)$, o-$C_6H_4(CF_3)(CN)$, p-$C_6H_4(CF_3)(CN)$, m-$C_6H_4(CF_3)(SO_3H)$, o-$C_6H_4(CF_3)(SO_3H)$, p-$C_6H_4(CF_3)(SO_3H)$, m-$C_6H_4(CF_3)(SO_3R)$, o-$C_6H_4(CF_3)(SO_3R)$, p-$C_6H_4(CF_3)(SO_3R)$, m-$C_6H_4(CF_3)(SO_3Q)$, o-$C_6H_4(CF_3)(SO_3Q)$, p-$C_6H_4(CF_3)(SO_3Q)$, m-$C_6H_4(F)(NO_2)$, o-$C_6H_4(F)(NO_2)$, p-$C_6H_4(F)(NO_2)$, m-$C_6H_4(COOH)(NO_2)$, o-$C_6H_4(COOH)(NO_2)$, p-$C_6H_4(COOH)(NO_2)$, m-$C_6H_4(CONH_2)(NO_2)$, o-$C_6H_4(CONH_2)(NO_2)$, p-$C_6H_4(CONH_2)(NO_2)$, m-$C_6H_4(COOCF_3)(NO_2)$, o-$C_6H_4(COOCF_3)(NO_2)$, p-$C_6H_4(COOCF_3)(NO_2)$, m-$C_6H_4(OOCCF_3)(NO_2)$, o-$C_6H_4(OOCCF_3)(NO_2)$, p-$C_6H_4(OOCCF_3)(NO_2)$, m-$C_6H_4(CN)(NO_2)$, o-$C_6H_4(CN)(NO_2)$, p-$C_6H_4(CN)(NO_2)$, m-$C_6H_4(SO_3H)(NO_2)$, o-$C_6H_4(SO_3H)(NO_2)$, p-$C_6H_4(SO_3H)(NO_2)$, m-$C_6H_4(SO_3R)(NO_2)$, o-$C_6H_4(SO_3R)(NO_2)$, p-$C_6H_4(SO_3R)(NO_2)$, m-$C_6H_4(SO_3Q)(NO_2)$, o-$C_6H_4(SO_3Q)(NO_2)$, p-$C_6H_4(SO_3Q)(NO_2)$, 1,2,3-$C_6H_3(CF_3)_2(NO_2)$, 1,3,4-$C_6H_3(CF_3)_2(NO_2)$, 1,3,5-$C_6H_3(CF_3)_2(NO_2)$, 1,2,3-$C_6H_3(CF_3)(NO_2)_2$, 1,3,4-$C_6H_3(CF_3)(NO_2)_2$, 1,3,5-$C_6H_3(CF_3)(NO_2)_2$, 1,2,3-$C_6H_3F_2(NO_2)$, 1,3,4-$C_6H_3F_2(NO_2)$, 1,3,5-$C_6H_3F_2(NO_2)$, 1,2,3-$C_6H_3(CF_3)F_2$, 1,3,4-$C_6H_3(CF_3)F_2$, 1,3,5-$C_6H_3(CF_3)F_2$, 1,2,3-$C_6H_3(COOH)_2(NO_2)$, 1,3,4-$C_6H_3(COOH)_2(NO_2)$, 1,3,5-$C_6H_3(COOH)_2(NO_2)$, 1,2,3-$C_6H_3(CF_3)(COOH)_2$, 1,3,4-$C_6H_3(CF_3)(COOH)_2$, 1,3,5-$C_6H_3(CF_3)(COOH)_2$, 1,2,3-$C_6H_3(CONH_2)_2(NO_2)$, 1,3,4-$C_6H_3(CONH_2)_2(NO_2)$, 1,3,5-$C_6H_3(CONH_2)_2(NO_2)$, 1,2,3-$C_6H_3(CF_3)(CONH_2)_2$, 1,3,4-$C_6H_3(CF_3)(CONH_2)_2$, 1,3,5-$C_6H_3(CF_3)(CONH_2)_2$, 1,2,3-$C_6H_3(COOCF_3)_2(NO_2)$, 1,3,4-$C_6H_3(COOCF_3)_2(NO_2)$, 1,3,5-$C_6H_3(COOCF_3)_2(NO_2)$, 1,2,3-$C_6H_3(CF_3)(COOCF_3)_2$, 1,3,4-$C_6H_3(CF_3)(COOCF_3)_2$, 1,3,5-$C_6H_3(CF_3)(COOCF_3)_2$, 1,2,3-$C_6H_3(OOCCF_3)_2(NO_2)$, 1,3,4-$C_6H_3(OOCCF_3)_2(NO_2)$, 1,3,5-$C_6H_3(OOCCF_3)_2(NO_2)$, 1,2,3-$C_6H_3(CF_3)(OOCCF_3)_2$, 1,3,4-$C_6H_3(CF_3)(OOCCF_3)_2$, 1,3,5-$C_6H_3(CF_3)(OOCCF_3)_2$, 1,2,3-$C_6H_3(CN)_2(NO_2)$, 1,3,4-$C_6H_3(CN)_2(NO_2)$, 1,3,5-$C_6H_3(CN)_2(NO_2)$, 1,2,3-$C_6H_3(SO_3H)(CN)_2$, 1,3,4-$C_6H_3(SO_3H)(CN)_2$, 1,3,5-$C_6H_3(SO_3H)(CN)_2$, 1,2,3-$C_6H_3(SO_3R)(CN)_2$, 1,3,4-$C_6H_3(SO_3R)(CN)_2$, 1,3,5-$C_6H_3(SO_3R)(CN)_2$, 1,2,3-$C_6H_3(SO_3Q)(CN)_2$, 1,3,4-$C_6H_3(SO_3Q)(CN)_2$, 1,3,5-$C_6H_3(SO_3Q)(CN)_2$, 1,2,3-$C_6H_3(CF_3)_2(SO_3H)$, 1,3,4-$C_6H_3(CF_3)_2(SO_3H)$, 1,3,5-$C_6H_3(CF_3)_2(SO_3H)$, 1,2,3-$C_6H_3(CF_3)_2(SO_3R)$, 1,3,4-$C_6H_3(CF_3)_2(SO_3R)$, 1,3,5-$C_6H_3(CF_3)_2(SO_3R)$, 1,2,3-$C_6H_3(CF_3)_2(SO_3Q)$, 1,3,4-$C_6H_3(CF_3)_2(SO_3Q)$, 1,3,5-$C_6H_3(CF_3)_2(SO_3Q)$, 1,2,3-$C_6H_3(CF_3)_3$, 1,3,4-$C_6H_3(CF_3)_3$, 1,3,5-$C_6H_3(CF_3)_3$, 1,2,3-$C_6H_3(NO_2)_3$, 1,3,4-$C_6H_3(NO_2)_3$, 1,3,5-$C_6H_3(NO_2)_3$, 1,2,3-$C_6H_3F_3$, 1,3,4-$C_6H_3F_3$, 1,3,5-$C_6H_3F_3$, 1,2,3-$C_6H_3(COOH)_3$, 1,3,4-$C_6H_3(COOH)_3$, 1,3,5-$C_6H_3(COOH)_3$, 1,2,3-$C_6H_3(COOCF_3)_3$, 1,3,4-$C_6H_3(COOCF_3)_3$, 1,3,5-$C_6H_3(COOCF_3)_3$, 1,2,3-$C_6H_3(OOCCF_3)_3$, 1,3,4-$C_6H_3(OOCCF_3)_3$, 1,3,5-$C_6H_3(OOCCF_3)_3$, 1,2,3-$C_6H_3(CN)_3$, 1,3,4-$C_6H_3(CN)_3$, 1,3,5-$C_6H_3(CN)_3$, 1,2,3-$C_6H_3(SO_3H)_3$, 1,3,4-$C_6H_3(SO_3H)_3$, 1,3,5-$C_6H_3(SO_3H)_3$, 1,2,3-$C_6H_3(SO_3R)_3$, 1,3,4-$C_6H_3(SO_3R)_3$, 1,3,5-$C_6H_3(SO_3R)_3$, 1,2,3-$C_6H_3(SO_3Q)_3$, 1,3,4-$C_6H_3(SO_3Q)_3$, 1,3,5-$C_6H_3(SO_3Q)_3$, 1,2,3-$C_6H_3(CONH_2)_3$, 1,3,4-$C_6H_3(CONH_2)_3$, and 1,3,5-$C_6H_3(CONH_2)_3$. As used herein, R is any aliphatic (e.g., $C_{1-8}$ alkyl, fluoro-$C_{1-8}$ alkyl), heteroaliphatic, aromatic, or heteroaromatic moiety, each of which is optionally substituted, and Q refers to a cation.

In certain embodiments, the non-oxidizable liquid is a nitroarene. As used herein, "nitroarene" refers to any deactivated arene comprising at least one nitro group. For example, the nitroarene can be nitro-substituted benzene, nitro-substituted toluene, nitro-substituted xylene, nitro-substituted naphthalene, nitro-substituted biphenyl, or nitro-substituted anthracene.

In some embodiments, the non-oxidizable liquid is one or more deactivated aliphatic(s). As used herein, "deactivated aliphatic" refers to at least one aliphatic group, as described herein, that has 1 or more electron withdrawing substituents (e.g., 2 or more, 3 or more, 4 or more, or 5 or more electron withdrawing substituents).

In some embodiments, the deactivated aliphatic non-oxidizable liquid is at least one saturated, unsaturated, branched, straight-chained, or cyclic $C_1$-$C_9$ alkyl aliphatic group that is substituted with at least 1 electron withdrawing substituent (e.g., 2 or more, 3 or more, 4 or more, or 5 or more electron withdrawing substituents). An exemplary, but non-limiting list of deactivated $C_1$-$C_9$ alkyl aliphatics is methyl, ethyl, n-propyl, iso-propyl, n-butyl, sec-butyl, tert-butyl, n-pentyl, sec-pentyl, neo-pentyl, hexyl, heptyl, octyl, nonyl, cyclopentyl, cyclohexyl, propenyl, 2-butenyl, 3-butenyl, 2-pentenyl, 3-pentenyl, 4-pentenyl, or a combination thereof, in which the $C_1$-$C_9$ alkyl is substituted with 1 or more electron withdrawing substituents.

In some instances, the deactivated aliphatic is methyl, ethyl, n-propyl, iso-propyl, n-butyl, sec-butyl, tert-butyl, n-pentyl, sec-pentyl, or neo-pentyl, in which the methyl, ethyl, n-propyl, iso-propyl, n-butyl, sec-butyl, tert-butyl, n-pentyl, sec-pentyl, or neo-pentyl is substituted with 1 or more electron withdrawing substituents. In certain embodiments, the deactivated aliphatic is methyl, ethyl, n-propyl, or iso-propyl in which the methyl, ethyl, n-propane, or iso-propyl is substituted with 1 or more electron withdrawing substituents.

In other embodiments, the deactivated aliphatic is trifluoromethanol, trifluoromethyl 2,2,2-trifluoroacetate, 2,2,2-trifluoroethan-1-ol, 2,2,2-trifluoroethyl 2,2,2-trifluoroacetate, perfluoroethyl 2,2,2-trifluoroacetate, 1,1,2,2,2-pentafluoroethan-1-ol, nitromethane, trifluoro(nitro)methane, 1,1,2,2-tetrafluoroethane-1,2-diol, 1,1,2,2-tetrafluoro-2-hydroxyethyl 2,2,2-trifluoroacetate, perfluoroethane-1,2-diyl bis(2,2,2-trifluoroacetate), ethane-1,2-diyl bis(2,2,2-trifluoroacetate), 1,1,2,2,3,3-hexafluoropropane-1,3-diol, propane-1,2,3-triyl tris(2,2,2-trifluoroacetate), oxalic acid, 1,1,1,4,4,4-hexafluorobutane-2,3-dione, methyl 2,2,2-trifluoroacetate, methyl 2,2,3,3,3-pentafluoropropanoate, or trifluoromethyl 2,2,3,3,3-pentafluoropropanoate.

In other embodiments, the deactivated aliphatic is trifluoromethyl acetate, 1,1-difluoroethyl acetate, 2,2,2-trifluoroethyl acetate, perfluoroethyl acetate, perfluoropropan-2-yl acetate, 1,1,1,3,3,3-hexafluoropropan-2-yl acetate, 1,1,2,2-tetrafluoro-2-hydroxyethyl acetate, perfluoroethane-1,2-diyl diacetate, ethane-1,2-diyl diacetate, propane-1,2,3-triyl trisacetate, perfluoropropane-1,2,3-triyl triacetate, 1,1,3,3-tetrafluoropropane-1,2,3-triyl triacetate, or 1,1-difluoroethane-1,2-diyl diacetate.

In some embodiments, the non-oxidizable liquid is one or more deactivated heteroarene(s). As used herein, "deactivated heteroarene" refers to at least one monocyclic or polycyclic heteroaromatic compound which has at least one heteroatom (O, S, or N) in at least one of the rings. The term "heteroaromatic" is as described herein.

In some embodiments, the deactivated heteroarene is isoxazole, oxazole, isothiazole, thiazole, imidazole, thiadiazole, tetrazole, triazole, oxadiazole, pyrazole, pyrazine, pyrimidine, or triazine, each of which is substituted or unsubstituted. In other preferred embodiments, the deactivated heteroarene is pyrrole, furan, thiophene, or pyridine, each of which is substituted with at least one substituent that is an electron withdrawing substituent.

In other embodiments, the deactivated heteroarene is perfluoroisoxazole, perfluorooxazole, perfluoroisothiazole, perfluorothiazole, perfluoroimidazole, perfluorothiadiazole, perfluorotetrazole, perfluorotriazole, perfluorooxadiazole, perfluoropyrazole, perfluoropyrazine, perfluorotriazine, perfluoropyrrole, perfluorofuran, perfluorothiophene, perfluoropyridine, nitropyrrole, nitrofuran, nitrothiophene, nitropyridine, cyanopyrrole, cyanofuran, cyanothiophene, cyanopyridine, picolinic acid, nicotinic acid, isonicotinic acid, pyridine sulfonic acid, pyrrole sulfonic acid, furan sulfonic acid, thiophene sulfonic acid, pyridine carboxylic acid, pyrrole carboxylic acid, furan carboxylic acid, thiophene carboxylic acid, trifluoromethyl pyridine, trifluoromethyl pyrrole, trifluoromethyl furan, or trifluoromethyl thiophene.

In some embodiments, the non-oxidizable liquid is one or more deactivated heteroaliphatic(s). The term "heteroaliphatic" is as described herein. In some embodiments, the heteroaliphatic compound is an ether, an ester, a carbonate, an amide, an amine, a carbamate, a thioether, a thioester, a phosphate, or a heterocycloalkane. The term "heterocycloalkane" refers to a cycloalkane, as described herein, in which at least one heteroatom (e.g., O, S, N, and/or P) replaces at least one carbon in the ring system. In an aspect, a heterocycloalkane is a 5-, 6-, or 7-membered monocyclic ring and contains one, two, or three heteroatoms selected from nitrogen, oxygen, and sulfur. Examples of such heterocycloalkane rings are pyrrolidine, pyrroline, pyran, piperidine, quinuclidine, imidazoline, dioxane, dioxolane, morpholine, thiomorpholine, trithiane, dithiane, pyrazoline, pyrazolidine, piperazine, or a combination thereof.

In certain embodiments, the deactivated heteroaliphatic has at least 1 electron withdrawing substituent. In some embodiments, the deactivated heteroaliphatic has at least 2 electron withdrawing substituents (e.g., at least 3, 4, 5, or 6 electron withdrawing substituents), such as those described herein.

For example, the deactivated heteroaliphatic compound can be trifluoro(trifluoromethoxy)methane, 1,1,1,2,2-pentafluoro-2-(trifluoromethoxy)ethane, 1,1,1,2,2-pentafluoro-2-(perfluoroethoxy)ethane, tris(trifluoromethyl)amine, 1,1,2,2,2-pentafluoro-N-(perfluoroethyl)-N-(trifluoromethyl)ethan-1-amine, tris(perfluoroethyl)amine, 2,2,2-trifluoro-N,N-bis(trifluoromethyl)acetamide, N,N-bis(trifluoromethyl)formamide, 2,2,2-trifluoroacetamide, perfluoropyrrolidine, perfluoropyrroline, perfluoropyran, perfluoropiperidine, perfluorodioxane, perfluoromorpholine, perfluoropiperazine, nitropyrrolidine, nitropyrroline, nitropyran, nitropiperidine, nitrodioxane, nitromorpholine, nitropiperazine, cyanopyrrolidine, cyanopyrroline, cyanopyran, cyanopiperidine, cyanodioxane, cyanomorpholine, cyanopiperazine, pyrrolidine carboxylic acid, pyrroline carboxylic acid, pyran carboxylic acid, piperidine carboxylic acid, dioxane carboxylic acid, morpholine carboxylic acid, piperazine carboxylic acid, pyrrolidine sulfonic acid, pyrroline sulfonic acid, pyran sulfonic acid, piperidine sulfonic acid, dioxane sulfonic acid, morpholine sulfonic acid, or piperazine sulfonic acid.

In some embodiments, the non-oxidizable liquid is one or more carbonate(s). The carbonate can be chemical compound comprising at least one carbonate moiety (e.g., 1 carbonate, 2 carbonates, 3 carbonates, or 4 carbonates). For example, the carbonate can be an alkyl carbonate, a heteroalkyl carbonate, a cycloalkyl carbonate, a heterocycloalkyl carbonate, an aryl carbonate, hydrogen carbonate, or a combination thereof.

In any of the embodiments described herein, the electron withdrawing substituent can be any suitable electron withdrawing group, such as —$NO_2$, fluoro-$C_{1-8}$ alkyl, —F, —OOCR, —$OH_2^+$, —COOH, —$CONH_2$, —COOR, —$NR_3^+$, —CN, —$SO_3H$, —$SO_3R$, —$SO_3W$, or a combination thereof, in which R is hydrogen or any aliphatic (e.g., $C_{1-8}$ alkyl, fluoro-$C_{1-8}$ alkyl), heteroaliphatic, aromatic, or heteroaromatic moiety, each of which is optionally substituted, and W is a cation comprising a metal selected from boron, bismuth, antimony, arsenic, lanthanum, cerium, scandium, yttrium, titanium, zirconium, hafnium, silver, zinc, cadmium, aluminum, gallium, indium, germanium, tin, phosphorus, an alkali metal, or an alkaline earth metal. In certain embodiments, R is —$CF_3$.

In some embodiments, the non-oxidizable liquid is the same as a product of the reaction described herein. For example, the non-oxidizable liquid can be the oxidized substrate (e.g., a product of the oxidation of propane can be 1,2-propane(trifluoroacetate), which is a deactivated heteroaliphatic).

In some embodiments, the liquid medium comprises a salt additive.

Generally, the salt additive is one or more compounds of the formula $Q_aZ_b$, in which Q is a cation, Z is a bridging oxide, a terminal oxide, a hydroxide, or an anion of the oxygen acid, a is an integer from 1 to 5 (i.e., 1, 2, 3, 4, or 5), b is an integer from 1 to 5 (i.e., 1, 2, 3, 4, or 5), and wherein a and b are the same or different and balance the oxidation states of Q and Z.

Q can be any suitable cation in any suitable oxidation state. In some embodiments, Q can be a proton, ammonium, a cation of an alkali metal, a cation of an alkaline earth metal, a cation of a rare-earth metal, a main group element cation, or a combination thereof. In some embodiments, Q is hydrogen or a cation of lithium, sodium, potassium, rubidium, cesium, francium, beryllium, magnesium, calcium, strontium, barium, or radium. Typically, Q has an oxidation state of +5, +4, +3, +2, or +1.

Z can be any suitable oxide (e.g., a bridging oxide or a terminal oxide), hydroxide, or anion of the oxygen acid, as described herein, in any suitable oxidation state. In some embodiments, Z is an anion of the oxygen acid that is one or more selected from an aliphatic carboxylate, heteroaliphatic carboxylate, aromatic carboxylate, heteroaromatic carboxylate, aliphatic sulfonate, heteroaliphatic sulfonate, aromatic sulfonate, heteroaromatic sulfonate, aliphatic phosphate, heteroaliphatic phosphate, aromatic phosphate, heteroaromatic phosphate, aliphatic borate, heteroaliphatic borate, aromatic borate, and heteroaromatic borate. In certain embodiments, Z is selected from a bridging oxide, a terminal oxide, hydroxide, sulfite, sulfate, hydrogen sulfate, thiosulfate, nitrite, nitrate, phosphite, phosphate, hydrogen phosphate, dihydrogen phosphate, carbonate, hydrogen carbonate, oxalate, cyanate, isocyanate, thiocyanate, carboxylate, sulfonate, and a combination thereof. As used herein, carboxylates can be alkylated variants (e.g., acetate), fluorinated variants (e.g., trifluoroacetate), or arylated variants (e.g., benzoates or benzoic acids). As used herein, "alkylated variants" and "arylated variants" refer to a carboxylic acid containing an alkyl group or an aryl group, respectively, as defined herein. Similarly, sulfonates can be alkylated variants (e.g., methanesulfonate) or fluorinated variants (e.g., trifluoromethanesulfonate). In certain embodiments, Z is one or more selected from trifluoroacetate, acetate, benzoate, sulfate, methanesulfonate, and trifluoromethanesulfonate. Typically, Z has an oxidation state of −4, −3, −2, or −1.

The oxygen acid in the context of the oxidizing electrophile and the oxygen acid in the context of the additive are each independently chosen. Accordingly, the oxygen acid in the context of the oxidizing electrophile and the oxygen acid in the context of the additive can be the same or different. Typically, the oxygen acid in the context of the oxidizing electrophile and the oxygen acid in the context of the additive are the same.

In preferred embodiments, the liquid medium and/or oxidizing composition comprises a salt of the oxygen acid.

In certain embodiments, X of the oxidizing electrophile formula $M^{+n}X_pL_q$ and Z of the additive are the same.

In certain embodiments, X of the oxidizing electrophile formula $M^{+n}X_pL_q$ and Z of the additive are different.

In some embodiments, $Q_aZ_b$ is a Brønsted acid, a salt, or a combination thereof. In some instances, $Q_aZ_b$ is one or more of acetic acid, ammonium acetate, lithium acetate, sodium acetate, potassium acetate, rubidium acetate, cesium acetate, francium acetate, beryllium acetate, magnesium acetate, calcium acetate, strontium acetate, barium acetate, radium acetate, benzoic acid, ammonium benzoate, lithium benzoate, sodium, potassium benzoate, rubidium benzoate, cesium benzoate, francium benzoate, beryllium benzoate, magnesium benzoate, calcium benzoate, strontium benzoate, barium benzoate, radium benzoate, trifluoroacetic acid, ammonium trifluoroacetate, lithium trifluoroacetate, sodium trifluoroacetate, potassium trifluoroacetate, trifluoroacetic acid, ammonium trifluoroacetate, lithium trifluoroacetate, sodium trifluoroacetate, potassium trifluoroacetate, rubidium trifluoroacetate, cesium trifluoroacetate, francium trifluoroacetate, beryllium trifluoroacetate, magnesium trifluoroacetate, calcium trifluoroacetate, strontium trifluoroacetate, barium trifluoroacetate, radium trifluoroacetate, sulfuric acid, ammonium sulfate, lithium sulfate, sodium sulfate, potassium sulfate, rubidium sulfate, cesium sulfate, francium sulfate, beryllium sulfate, magnesium sulfate, calcium sulfate, strontium sulfate, barium sulfate, radium sulfate, phosphoric acid, methanesulfonic acid, ammonium methanesulfonate, lithium methanesulfonate, sodium methanesulfonate, potassium methanesulfonate, rubidium methanesulfonate, cesium methanesulfonate, francium methanesulfonate, beryllium methanesulfonate, magnesium methanesulfonate, calcium methanesulfonate, strontium methanesulfonate, barium methanesulfonate, radium methanesulfonate, trifluoromethanesulfonic acid, ammonium trifluoromethanesulfonate, lithium trifluoromethanesulfonate, sodium trifluoromethanesulfonate, potassium trifluoromethanesulfonate, rubidium trifluoromethanesulfonate, cesium trifluoromethanesulfonate, francium trifluoromethanesulfonate, beryllium trifluoromethanesulfonate, magnesium trifluoromethanesulfonate, calcium trifluoromethanesulfonate, strontium trifluoromethanesulfonate, barium trifluoromethanesulfonate, or radium trifluoromethanesulfonate. In preferred embodiments, $Q_aZ_b$ is trifluoroacetic acid, acetic acid, benzoic acid, methanesulfonic acid, or a combination thereof, each of which can be substituted or unsubstituted.

In some embodiments, the liquid medium and/or oxidizing composition comprises a Lewis Acid. Generally, the Lewis acid is of formula $Q_aZ_b$, wherein $Q_aZ_b$ is any suitable, non-halide containing Lewis acid, which is a strong electron pair acceptor. In embodiments where $Q_aZ_b$ is a non-halide containing Lewis acid, Q can be a cation of a transition metal, a cation of a rare-earth metal, a main group cation, or a combination thereof. In some embodiments, Q is a cation of boron, bismuth, antimony, arsenic, lanthanum, cerium, scandium, yttrium, titanium, zirconium, hafnium, silver, zinc, cadmium, aluminum, gallium, indium, germanium, tin, phosphorus, or a combination thereof. Typically, Q has an oxidation state of +5, +4, +3, +2, or +1. In certain embodiments, Q is In(III), Sc(III), Zn(II), Ti(IV), Al(III), Ga(III), B(III), Sb(III), Bi(III), or As(III). It will be understood that any one or more Q(s) can be combined with any one or more Z(s), such that fundamental chemical rules are satisfied, to form the non-halide containing Lewis acid (e.g., Ce(OAc)$_3$, Ce(OTf)$_3$, Zn(OAc)$_2$, Zn(OTf)$_2$, ZnO, In(OAc)$_3$, In(OTf)$_3$, In$_2$O$_3$, Sb(OAc)$_3$, Sb(OTf)$_3$, Sb$_2$O$_3$, Bi(OAc)$_3$, Bi(OTf)$_3$, Bi$_2$O$_3$, Al(OTf)$_3$, Ga(OTf)$_3$, Sc(OAc)$_3$, Sc(OTf)$_3$, or Sc(OMs)$_3$). As used herein, "OTf" refers to trifluoromethanesulfonate, "OMs" refers to mesylate, and "OAc" refers to acetate.

In some embodiments, the liquid medium and/or oxidizing composition does not contain a halide ion (e.g., Cl$^-$, Br$^-$, or I$^-$). As used herein, the term "halide ion" is considered different from the term halogen atom. In particular, the term halide ion does not encompass a halogen atom (e.g., a fluorine atom, a chlorine atom, a bromine atom, or an iodine atom) attached to an aliphatic or aromatic substituent (i.e., a substituent that will not decompose to form free ions under reaction conditions). For example, iodine can be present in aromatic-iodine species, as this form of iodine would not be considered a halide ion. Instead, the term "halide ion" refers to ions of salt additives, such as alkali halide compounds (e.g., NaI, KCl, etc.). Accordingly, the halide ion can be present in the liquid medium and/or oxidizing composition in an amount less than 0.1 mol % (e.g., less than 0.05 mol %, less than 0.01 mol %, less than 0.005 mol %, less than 0.001 mol %) or about 0 mol % of the main group element.

In some embodiments, the liquid medium and/or oxidizing composition comprises a trace amount of a halide ion (e.g., $Cl^-$, $Br^-$, or $I^-$). It is possible that impurities in starting materials or from reactor corrosion can be responsible for the presence of trace halide ions. Accordingly, the halide ion can be present in an amount of about 0.00001 mol % of the main group element or more (e.g., about 0.0001 mol % or more, about 0.001 mol % or more, 0.01 mol % or more, 0.1 mol % or more, or about 1 mol % or more). Alternatively, or in addition, the halide ion can be present in an amount of about 5 mol % of the main group element or less (e.g., about 4 mol % or less, about 3 mol % or less, about 2 mol % or less, about 1 mol % or less, or about 0.1 mol % or less). Any two of the foregoing endpoints can be used to define a close-ended range, or any single endpoint can be used alone to define an open-ended range.

In some embodiments, the additive is water.

In some embodiments, the process comprises separating one or more components from the liquid medium. The one or more components can be separated by any suitable means, such as by filtration, distillation, flashing, rectifying, stripping, evaporation, absorption, adsorption, column chromatography, crystallization, centrifugation, extraction, recrystallization, membrane separation, or any combination thereof.

Distillation can be used to separate components of the liquid medium based on differences in the volatilities of the mixture components. A distillation process may optionally include a chemical reaction. An example of distillation is the removal of water and glycol products from a mixture of higher boiling components including an oxidizing electrophile in solution.

Flashing can be used to remove one or more light components from the liquid medium. Flashing is the partial vaporization that occurs when the pressure of a liquid stream is reduced. A typical flashing process includes a flow restriction such as a control valve followed by a vessel (i.e. flash drum) to allow for de-entrainment of liquid from a gas stream. Additional heating or cooling is optional. A flashing operation can be combined with chemical reactions. Upon flashing, the vapor phase is richer in the more volatile components compared to the remaining liquid phase. An adiabatic flashing process results in lower temperatures of outlet streams in comparison to the inlet feed. An example of flashing is the removal of light hydrocarbons, dissolved gases, and a portion of the light components from a liquid mixture that includes a metal (e.g., thallium) species in solution.

Rectifying can be used to remove one or more heavier components from a vapor stream by contacting with a liquid stream. The less volatile components concentrate in the liquid stream. It is possible to contact the two streams by using a packed column, trayed column, bubble column, or centrifugal contactor. Flows can be co-current or counter-current. Rectifying can optionally be combined with chemical reactions. An example of rectifying is the removal of ester reaction products from a vapor stream by contacting with a liquid stream.

Stripping can be used to remove one or more lighter components from a liquid stream by contacting with a vapor stream. The more volatile components concentrate in the vapor stream. It is possible to contact the two streams by using a packed column, trayed column, bubble column, or centrifugal contactor. Flows can be co-current or counter-current. Vapor streams used for stripping could include steam, air, nitrogen, process streams, and/or other suitable species to achieve the desired separation. Stripping can optionally be combined with chemical reactions. An example of stripping is the removal of lighter reaction products from the liquid phase by contacting with a gas stream.

Evaporation can be used to remove lighter components by vaporization at a liquid/vapor interface. Evaporator designs may include falling film, rising film, wiped film, plate, and multi-effect evaporators. An evaporation process can optionally be combined with chemical reactions. An example of an evaporation process is the removal of acetic acid and water from a mixture of heavier liquid components, including an antimony species in solution.

Absorption (scrubbing) can be used to selectively dissolve one or more components of a gas mixture into a liquid phase. It is possible to contact the two streams by using a packed column, trayed column, bubble column, or centrifugal contactor. If a chemical reaction occurs, the process is called chemical absorption. The liquid is selected to target the desired separation. An example of absorption is the removal of water from a vapor recycle stream by contacting with a glycol mixture.

Adsorption can be used to selectively remove one or more components of a stream based on physical or chemical interactions with a solid surface. If a chemical reaction occurs, the process is called chemisorption. The solid is selected to target the desired separation. An example of adsorption is the removal of water from a liquid recycle stream using a narrow-pore silica.

Extraction (partitioning) can be used to selectively remove one or more components from a liquid phase by contacting with a second liquid phase. Due to differences in solubilities in the two liquid phases, there can be a net transfer of species from one phase to the other. An extraction process can optionally be combined with chemical reactions. An example of extraction is contacting reactor effluent with a secondary phase that selectively dissolves a specific reaction product.

Membrane separations can be used to selectively remove one or more components from a fluid stream including gases and liquids. For example, pervaporation is a process for separating one or more components from a liquid stream by partial vaporization through a porous or non-porous membrane. Vapor permeation is a process for separating one or more components from a vapor stream by utilizing a porous or non-porous membrane. The membrane materials are selected based on their different permeabilities for different components. Membrane separations can optionally be combined with chemical reactions. An example of membrane separation is the removal of water from the organic reaction mixture using a selective ceramic membrane.

The above processes can be combined to separate components of the liquid medium, for example, membrane distillation or extractive distillation.

In some embodiments, the process comprises (b) separating the oxygenate and the reduced form of the oxidizing electrophile. The oxygenate and the reduced form of the oxidizing electrophile can be separated by any suitable method, such as the methods described herein. For example, the oxygenate and the reduced form of the oxidizing electrophile can be separated by distillation.

The present invention further encompasses a process comprising (c) hydrolyzing the oxygenate to form an alcohol, a diol (i.e., glycol), a polyol with three or more hydroxyl groups (e.g., a triol or tetraol), or a combination thereof. In preferred embodiments, a diol (i.e., glycol) is formed. As used herein, the term "hydrolyzing" refers to a class of organic chemical reactions in which an ester is converted into two separate molecules comprising an alcohol functionality and an acid functionality, usually through the action of acids and/or bases. Generally, the hydrolysis reaction forms an alcohol and a conjugate anion of the oxygen acid. The hydrolysis reaction can occur by any suitable method. For example, acids, bases, metals, heating, or a combination thereof can be used to perform the hydrolysis reaction.

In some embodiments, the hydrolysis step takes place in the presence of an acid capable of facilitating the hydrolysis reaction. As used herein, the phrase "facilitating the hydrolysis reaction" refers to lowering the activation energy necessary for the hydrolysis. In some embodiments, the acid is an oxygen acid, including those described herein.

In some embodiments, the hydrolysis step takes place in the presence of a base capable of facilitating the hydrolysis reaction. In some embodiments, the base is a conjugate anion of an oxygen acid described herein. In certain embodiments, a stronger base, such as an alkali metal or alkaline earth metal hydroxide, is required to facilitate the hydrolysis reaction.

The process can further comprise separating the alcohol, the diol (i.e., glycol), or the polyol with three or more hydroxyl groups (e.g., triol or tetraol) and the oxygen acid by any suitable method (e.g., filtration, distillation, column chromatography, crystallization, centrifugation, extraction, recrystallization, or a combination thereof). In some embodiments, the separated oxygen acid is recycled for use in step (a), as described herein.

In some embodiments, the process further comprises (d) contacting the reduced form of the oxidizing electrophile and any suitable oxidizing regeneration reagent to regenerate the oxidizing electrophile. Typically, the term "oxidant" is used in the context of generating the oxidizing electrophile and the phrase "oxidizing regeneration reagent" is used in the context of regenerating the oxidizing electrophile. However, the oxidant and the oxidizing regeneration reagent can be used interchangeably, and refer to a chemical moiety used to convert the reduced form of the oxidizing electrophile to the oxidizing electrophile. The oxidizing regeneration reagent can be the same as or different from the oxidant. For example, the oxidizing regeneration reagent can be a quinone, molecular oxygen, air, a peroxide, nitric oxide, nitrous oxide, nitric acid, a nitroxide, sulfur trioxide, ozone, or a combination thereof. The peroxide can be an organic peroxide, inorganic peroxide, hydrogen peroxide, or a combination thereof. In some embodiments, the oxidizing regeneration reagent can be an organic oxidant, such as a quinone or a nitroxide. In certain preferred embodiments, the oxidizing regeneration reagent is molecular oxygen, air, ozone, hydrogen peroxide, organoperoxide, nitric acid, or a combination thereof.

In some embodiments, step (d) is an electrochemical process. As used herein, an "electrochemical process" refers to a process comprising electron transfer to or from a molecule or ion using, for example, an electric current and/or an external voltage.

Thus, the process for oxidizing the alkene can comprise the oxidizing regeneration reagent, the oxidant, both the oxidizing regeneration reagent and the oxidant, or neither the oxidizing regeneration reagent nor the oxidant.

In some embodiments, the process for oxidizing the alkene comprises neither the oxidizing regeneration reagent nor the oxidant. Accordingly, the oxidizing regeneration reagent and the oxidant can be present in an amount of 0 mol % (e.g., below the level of detection) of the main group element.

In some embodiments, the oxidizing regeneration reagent and/or the oxidant are present in the liquid medium. The amount of the oxidizing regeneration reagent and/or the oxidant is not particularly limited such that a sufficient amount of the oxidizing electrophile is maintained to oxidize the alkene. Accordingly, the oxidizing regeneration reagent and/or the oxidant can be present in an amount of about 0.1 mol % of the alkene or more (e.g., about 0.2 mol % or more, about 0.3 mol % or more, about 0.4 mol % or more, about 0.5 mol % or more, about 1 mol % or more, about 2 mol % or more, about 3 mol % or more, about 5 mol % or more, about 10 mol % or more, about 20 mol % or more, about 50 mol % or more, or about 100 mol % or more). Alternatively, or in addition, the oxidizing regeneration reagent and/or the oxidant can be present in an amount of about 2000 mol % of the alkene or less (e.g., about 1500 mol % or less, about 1000 mol % or less, about 900 mol % or less, about 800 mol % or less, about 700 mol % or less, about 600 mol % or less, about 500 mol % or less, about 400 mol % or less, about 300 mol % or less, about 200 mol % or less, or about 100 mol % or less). Any two of the foregoing endpoints can be used to define a close-ended range, or any single endpoint can be used alone to define an open-ended range.

In some embodiments, the reduced form of the oxidizing electrophile and the oxidizing regeneration reagent are contacted to regenerate the oxidizing electrophile in the presence of an oxidative regeneration catalyst. The oxidative regeneration catalyst can be any suitable catalyst, such as an oxidative regeneration catalyst that comprises copper, silver, iron, cobalt, manganese, nickel, chromium, vanadium, or a combination thereof.

In certain embodiments, the oxidizing regeneration reagent oxidizes the reduced form of the oxidizing electrophile to the oxidizing electrophile in the liquid medium in the presence of the alkene. In certain embodiments, the oxidizing regeneration reagent oxidizes the reduced form of the oxidizing electrophile to the oxidizing electrophile in a separate reactor, and is added back to the liquid medium. Accordingly, the regenerated oxidizing electrophile can be recycled for use in step (a), as described herein.

The process for oxidizing the alkene can further comprise recycling any of the components, that are not consumed in the process, to be reused in the process (e.g., recycling to be reused in the liquid medium and/or the oxidizing composition). For example, the substrate, oxidizing electrophile, non-oxidizable liquid, additive, or any combination thereof can be recycled and reused in the process.

In some instances, the process for oxidizing an alkene comprises the oxidizing electrophile and/or the reduced form of an oxidizing electrophile, and liquid medium as a heterogeneous mixture or a homogenous mixture.

As used herein, the phrase "homogeneous mixture" refers to a uniform composition containing one or more phases, e.g., liquid/liquid, liquid/solid, liquid/gas, solid/gas, or liquid/solid/gas. Thus, a homogeneous mixture comprising a liquid can also contain a gas and/or a solid, only if the gas and/or the solid is soluble in the liquid as to form a uniform composition. In embodiments where the liquid medium is a homogeneous mixture, the oxidizing electrophile and/or the reduced form of an oxidizing electrophile are soluble in the liquid medium.

In preferred embodiments, the liquid medium is a homogeneous mixture. In other preferred embodiments, the liquid medium is a heterogeneous mixture, wherein any component can be insoluble in the liquid medium, as long as the oxidizing electrophile maintains a certain level of solubility. Without wishing to be bound by any particular theory, it is believed that the reaction is more efficient when at least the oxidizing electrophile is soluble in the liquid medium. In some embodiments, the liquid medium can transition from a homogeneous mixture to a heterogeneous mixture and from a heterogeneous mixture to a homogeneous mixture.

In some embodiments, the oxidizing electrophile maintains a level of solubility such that about 25% or less of the total mass of the oxidizing electrophile is an insoluble solid in the mixture (e.g., about 20% or less, about 15% or less, about 10% or less, about 5% or less, or about 1% or less). Alternatively, the oxidizing electrophile can be completely soluble in the liquid medium (e.g., about 0% of the total mass of the oxidizing electrophile is an insoluble solid in the mixture). Thus, the oxidizing electrophile maintains a level of solubility such that about 0% to about 25% of the total mass of the oxidizing electrophile is an insoluble solid in the mixture (e.g., about 0% to about 20%, about 0% to about 15%, about 0% to about 12%, about 0% to about 10%, about 0% to about 5%, or about 0% to about 1%).

As used herein, the phrase "insoluble solid" refers to any solid that does not readily dissolve in the liquid medium as to form a uniform composition. The amount of insoluble solid can be determined by any suitable means. For example, the amount of insoluble solid can be filtered from the liquid medium using microfiltration (i.e., filters ranging from about 0.1 microns to about 1.0 micron). Accordingly, the percentage of total mass of the oxidizing electrophile that exists as an insoluble solid in the mixture can be determined by the mass of insoluble oxidizing electrophile filtered from the liquid medium using microfiltration divided by the theoretical total mass of the oxidizing electrophile in the mixture.

In some embodiments, regardless of whether the mixture is heterogeneous or homogeneous, the reduced form and oxidized form of the electrophile comprising the main group element are soluble in the liquid medium. Accordingly, the mixture is substantially free (e.g., about 0 mass % and/or below the level of detection) of a solid comprising the main group element.

The process for oxidizing an alkene can be carried out in a single reactor or carried out in at least 2 reactors (e.g., at least 3 or at least 4 reactors). When the process is carried out in a single reactor and the oxidizing electrophile is present in at least a stoichiometric quantity, the process for oxidizing an alkene does not necessitate regeneration of the oxidizing electrophile. In this embodiment, the process for oxidizing an alkene can be carried out under a single set of conditions in the single reactor.

Alternatively, the process can be carried out in a single reactor, in which the reactor is operated under conditions suitable for oxidizing the alkene using the oxidizing electrophile and simultaneous regeneration of the oxidizing electrophile by contacting the electrophile reduction product and the oxidizing regeneration reagent. For example, when the oxidizing electrophile is depleted, the oxidizing regeneration reagent, optionally in the presence of an oxidative regeneration catalyst, is present in the liquid medium to regenerate the oxidizing electrophile.

In some embodiments, the process can be carried out in a single reactor in a sequential manner. For example, the reactor can be operated first under conditions suitable for oxidizing the alkene to an oxygenate using the oxidizing electrophile and optionally hydrolyzing the oxygenate, then subsequently operated under conditions suitable for regeneration of the oxidizing electrophile by contacting the electrophile reduction product and the oxidizing regeneration reagent. For example, the oxidizing electrophile can be immobilized within the reactor, in which first a mixture comprising the alkene is circulated, then, when the oxidizing electrophile is depleted, a mixture comprising the oxidizing regeneration reagent, optionally in the presence of an oxidative regeneration catalyst, is circulated to regenerate the oxidizing electrophile.

Alternatively, the process can be carried out in a two reactor circulating liquid phase system, in which the reaction of the alkene and the oxidizing electrophile and optionally hydrolyzing the oxygenate is carried out in a first reactor, and the reaction of the electrophile reduction product and the oxidizing regeneration reagent used to regenerate the oxidizing electrophile is carried out in a second reactor.

Alternatively, the process can be carried out in a three reactor circulating liquid phase system, in which the reaction of the alkene to the oxygenate is carried out in a first reactor, the hydrolyzing the oxygenate is carried out in a second reactor, and the reaction of the electrophile reduction product and the oxidizing regeneration reagent used to regenerate the oxidizing electrophile is carried out in a third reactor.

The process of the present invention can take place at any temperature suitable for forming an oxygenate, and ultimately, forming a glycol. In some embodiments, the process for oxidizing an alkene can be performed at less than about 300° C., for example, less than about 285° C., less than about 275° C., less than about 260° C., less than about 250° C., less than about 225° C., less than about 200° C., less than about 150° C., or less than about 140° C. Alternatively, or in addition to, the process for oxidizing an alkene can be performed at greater than about 50° C., for example, greater than about 70° C., greater than about 80° C., greater than about 100° C., greater than about 120° C., greater than about 140° C., greater than about 150° C., greater than about 160° C., greater than about 170° C., greater than about 180° C., greater than about 190° C., or greater than about 200° C. Any two of the foregoing endpoints can be used to define a close-ended range, or one endpoint can be used alone to define an open-ended range. Thus, the process can be performed at a temperature between about 50° C. to about 300° C., for example, about 50° C. to about to about 275° C., about 50° C. to about 250° C., about 50° C. to about 225° C., about 50° C. to about 200° C., about 70° C. to about 200° C., about 80° C. to about 200° C., about 70° C. to about 140° C., about 100° C. to about 200° C., about 120° C. to about 200° C., about 140° C. to about 200° C., about 150° C. to about 200° C., about 160° C. to about 200° C., about 170° C. to about 200° C., about 180° C. to about 200° C., about 190° C. to about 200° C., about 200° C. to about 300° C., about 200° C. to about 350° C., about 100° C. to about 300° C., or about 150° C. to about 250° C. In some embodiments, the temperature is between about 50° C. to about 300° C., and more preferably, between about 70° C. to about 140° C.

The process of the present invention can take place at any pressure suitable for forming an oxygenate, and ultimately, forming a glycol. In some embodiments, the process for oxidizing an alkene can be performed at less than about 2000 psi (about 13800 kPa), for example, less than about 1500 psi (about 10300 kPa), less than about 1000 psi (about 6900 kPa), less than about 500 psi (about 3450 kPa), less than about 400 psi (about 2800 kPa), less than about 300 psi (about 2100 kPa), or less than about 200 psi (about 1400 kPa). Alternatively, or in addition to, the process for oxidizing an alkene can be performed at greater than about 0 psi (about 0 kPa), for example, greater than about 1 psi (about 6.9 kPa), greater than about 2 psi (about 13.8 kPa), greater than about 3 psi (about 20.7 kPa), greater than about 4 psi (about 27.6 kPa), greater than about 5 psi (about 34.5 kPa), greater than about 10 psi (about 69 kPa), or greater than about 20 psi (about 138 kPa). Any two of the foregoing endpoints can be used to define a close-ended range, or one endpoint can be used alone to define an open-ended range. Thus, the process can be performed at a pressure between about 0 psi (about 0 kPa) to about 2000 psi (about 13800 kPa), for example, about 0 psi (about 0 kPa) and about 1500 psi (about 10300 kPa), about 0 psi (about 0 kPa) and about 1000 psi (about 6900 kPa), about 0 psi (about 0 kPa) and about 500 psi (about 3450 kPa), about 0 psi (about 0 kPa) and about 400 psi (about 2800 kPa), about 0 psi (about 0 kPa) and about 300 psi (about 2100 kPa), about 0 psi (about 0 kPa) and about 200 psi (about 1400 kPa), about 2 psi (about 13.8 kPa) and about 1500 psi (about 10300 kPa), about 2 psi (about 13.8 kPa) and about 1000 psi (about 6900 kPa), about 2 psi (about 13.8 kPa) and about 500 psi (about 3450 kPa), about 2 psi (about 13.8 kPa) and about 400 psi (about 2800 kPa), about 2 psi (about 13.8 kPa) and about 300 psi (about 2100 kPa), about 2 psi (about 13.8 kPa) and about 200 psi (about 1400 kPa), about 5 psi (about 34.5 kPa) and about 1500 psi (about 10300 kPa), about 5 psi (about 34.5 kPa) and about 1000 psi (about 6900 kPa), about 5 psi (about 34.5 kPa) and about 500 psi (about 3450 kPa), about 5 psi (about 34.5 kPa) and about 400 psi (about 2800 kPa), about 5 psi (about 34.5 kPa) and about 300 psi (about 2100 kPa), or about 5 psi (about 34.5 kPa) and about 200 psi (about 1400 kPa), In some embodiments, the pressure is between about 2 psi (about 13.8 kPa) and about 500 psi (about 3450 kPa), and more preferably, between about 5 psi (about 34.5 kPa) and about 200 psi (about 1400 kPa).

The invention is further illustrated by the following embodiments.

(1) A process for oxidizing an alkene, comprising: (a) contacting an alkene, and either (i) an oxidizing electrophile comprising a main group element in oxidized form, or (ii) an oxidant and a reduced form of the oxidizing electrophile, in a liquid medium comprising an oxygen acid and optionally one or more additives selected from a non-oxidizable liquid, a salt additive, a Lewis acid, and water, to provide an oxygenate and a reduced form of the oxidizing electrophile; and (b) optionally separating the oxygenate and the reduced form of the oxidizing electrophile.

(2) The process of embodiment (1), comprising (b) separating the oxygenate and the reduced form of the oxidizing electrophile.

(3) The process of embodiment (1) or embodiment (2), wherein the oxygenate comprises one or more alcohol functionalities, one or more ester functionalities, or a combination thereof.

(4) The process of any one of embodiments (1)-(3), further comprising (c) hydrolyzing the oxygenate to form an alcohol, a diol, a polyol with three or more hydroxyl groups, or a combination thereof.

(5) The process of embodiment (4), wherein a diol is formed.

(6) The process of embodiment (4) or embodiment (5), wherein the hydrolysis step takes place in the presence of an acid.

(7) The process of embodiment (4) or embodiment (5), wherein the hydrolysis step takes place in the presence of a base.

(8) The process of any one of embodiments (1)-(7), wherein the alkene is a $C_2$-$C_{20}$ alkene, a $C_2$-$C_2O$ heteroalkene, $C_3$-$C_{20}$ cycloalkene, $C_3$-$C_{20}$ heterocycloalkene, arylalkene, heteroarylalkene, or a combination thereof.

(9) The process of embodiment (8), wherein the alkene is ethene, propene, or a mixture thereof.

(10) The process of any one of embodiments (1)-(9), wherein the oxidizing electrophile comprises thallium, lead, antimony, mercury, tin, selenium, tellurium, arsenic, iodine, or bismuth.

(11) The process of embodiment (10), wherein the oxidizing electrophile comprises Sb(V), Te(VI), Te(IV), Bi(V), Se(VI), Se(IV), As(V), I(V), I(III), or Sn(IV).

(12) The process of any one of embodiments (1)-(11), wherein the oxidizing electrophile comprises at least one conjugate anion of an oxygen acid.

(13) The process of embodiment (12), wherein the conjugate anion of the oxygen acid is an aliphatic carboxylate, heteroaliphatic carboxylate, aromatic carboxylate, heteroaromatic carboxylate, aliphatic sulfonate, heteroaliphatic sulfonate, aromatic sulfonate, heteroaromatic sulfonate, aliphatic phosphate, heteroaliphatic phosphate, aromatic phosphate, heteroaromatic phosphate, aliphatic borate, heteroaliphatic borate, aromatic borate, heteroaromatic borate, or a mixture thereof.

(14) The process of embodiment (12), wherein the conjugate anion of the oxygen acid is trifluoroacetate, acetate, alkylsulfonate, phosphate, nitrate, sulfate, trifluoromethanesulfate, or fluorosulfate.

(15) The process of any one of embodiments (12)-(14), wherein the oxidizing electrophile further comprises at least one ligand with at least one electron-withdrawing group.

(16) The process of embodiment (15), wherein the ligand with at least one electron-withdrawing group is selected from

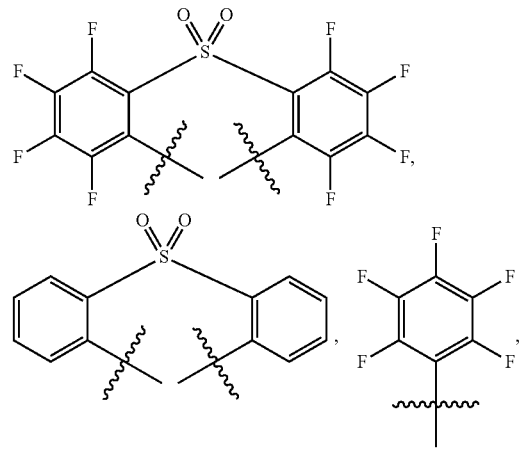

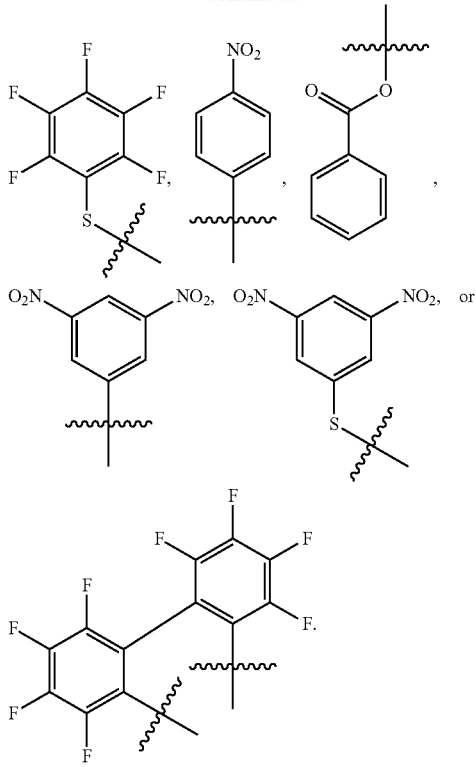

(17) The process of any one of embodiments (1)-(16), wherein the oxidizing electrophile has a formula $M^{+n}X_pL_q$, wherein M is a main group element cation in an oxidation state of n, X is the conjugate anion of an oxygen acid, L is a ligand, n is an integer from 2 to 6, p is an integer from 1 to 6, and q is an integer from 0 to 5.

(18) The process of embodiment (17), wherein $M^{+n}X_pL_q$ undergoes reaction with the alkene in the liquid medium to yield a reduced form of the oxidizing electrophile of formula $M^{+(n-2)}X_{p-2}L_q$ or $M^{+(n-1)}X_{p-1}L_q$.

(19) The process of any one of embodiments (1)-(18), wherein the oxidizing electrophile comprising a main group element is present in at least stoichiometric quantities relative to the amount of oxygenate produced.

(20) The process of any one of embodiments (1)-(18), wherein the oxidizing electrophile comprising a main group element in oxidized form is present in less than stoichiometric quantities relative to the alkene and acts as a catalyst.

(21) The process of embodiment (20), further comprising (d) contacting the reduced form of the oxidizing electrophile and an oxidizing regeneration reagent to regenerate the oxidizing electrophile.

(22) The process of embodiment (21), wherein the oxidizing regeneration reagent is a quinone, molecular oxygen, air, a peroxide, nitric oxide, nitrous oxide, nitric acid, a nitroxide, sulfur trioxide, ozone, or a combination thereof.

(23) The process of embodiment (21), wherein step (d) is an electrochemical process.

(24) The process of embodiment (22) or embodiment (23), wherein the reduced form of the oxidizing electrophile and the oxidizing regeneration reagent are contacted to regenerate the oxidizing electrophile in the presence of an oxidative regeneration catalyst.

(25) The process of embodiment (24), wherein the oxidative regeneration catalyst comprises copper, silver, iron, cobalt, manganese, nickel, chromium, vanadium, or a combination thereof.

(26) The process of any one of embodiments (22)-(25), wherein the oxidizing regeneration reagent oxidizes the reduced form of the oxidizing electrophile to the oxidizing electrophile in the liquid medium in the presence of the alkene.

(27) The process of any one of embodiments (1)-(26), wherein the oxygen acid is aliphatic carboxylic acid, heteroaliphatic carboxylic acid, aromatic carboxylic acid, heteroaromatic carboxylic acid, aliphatic sulfonic acid, heteroaliphatic sulfonic acid, aromatic sulfonic acid, heteroaromatic sulfonic acid, aliphatic phosphonic acid, heteroaliphatic phosphonic acid, aromatic phosphonic acid, heteroaromatic phosphonic acid, boric acid, aliphatic boronic acid, heteroaliphatic boronic acid, aromatic boronic acid, heteroaromatic boronic acid, or a mixture thereof.

(28) The process of any one of embodiments (1)-(26), wherein the oxygen acid is trifluoroacetic acid, acetic acid, methanesulfonic acid, phosphoric acid, nitric acid, sulfuric acid, trifluoromethanesulfonic acid, fluorosulfuric acid, or a mixture thereof.

(29) The process of any one of embodiments (1)-(28), wherein all or a portion of the oxygen acid is added as an anhydride of the oxygen acid.

(30) The process of any one of embodiments (1)-(29), wherein the liquid medium comprises a non-oxidizable liquid selected from a fluorinated hydrocarbon, a sulfone, a deactivated arene, a deactivated aliphatic, a deactivated heteroarene, a deactivated heteroaliphatic, or a combination thereof, wherein the non-oxidizable liquid is substantially inert in the presence of the oxidizing electrophile.

(31) The process of any one of embodiments (1)-(30), wherein the liquid medium comprises a salt additive of formula $Q_aZ_b$, wherein Q is a cation, Z is a bridging oxide, a terminal oxide, a hydroxide, or a conjugate anion of an oxygen acid, a is an integer from 1 to 5, and b is an integer from 1 to 5, wherein a and b are the same or different and balance the oxidation states of Q and Z.

(32) The process of embodiment (31), wherein Z is a conjugate anion of an oxygen acid that is one or more selected from an aliphatic carboxylate, heteroaliphatic carboxylate, aromatic carboxylate, heteroaromatic carboxylate, aliphatic sulfonate, heteroaliphatic sulfonate, aromatic sulfonate, heteroaromatic sulfonate, aliphatic phosphate, heteroaliphatic phosphate, aromatic phosphate, heteroaromatic phosphate, aliphatic borate, heteroaliphatic borate, aromatic borate, heteroaromatic borate, and a combination thereof.

(33) The process of embodiment (31) or embodiment (32), wherein Q is a proton, a cation of an alkali metal, a cation of an alkaline earth metal, a cation of a rare-earth metal, a main group element cation, or a combination thereof.

(34) The process of any one of embodiments (1)-(33), wherein the liquid medium comprises a Lewis acid.

(35) The process of any one of embodiments (1)-(34), wherein the reaction temperature in (a) is from about 50° C. to about 300° C.

(36) The process of any one of embodiments (1)-(35), wherein the reaction pressure in (a) is between about 2 psi (about 13.8 kPa) and about 500 psi (about 3450 kPa).

The following examples further illustrate the invention but, of course, should not be construed as in any way limiting its scope.

EXAMPLE 1

This example demonstrates the conversion of ethylene to ethylene glycol with an oxidizing electrophile.

Oxidizing electrophile, $Sb^V(TFA)_5$, was prepared by either (i) reacting $[Sb(OMe)_5]_2$ dinuclear complex with trifluoroacetic anhydride (TFAA), followed by dilution with trifluoroacetic acid (HTFA), or (ii) oxidizing $Sb(TFA)_3$ with hydrogen peroxide ($H_2O_2$), as shown in Eq. 4 and Eq. 5, respectively:

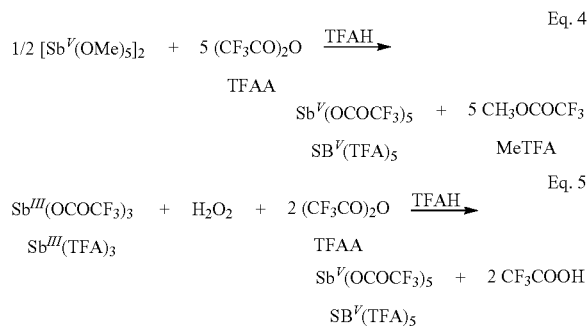

Figure 4:
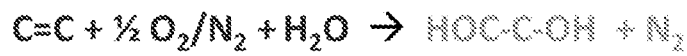
FIG. 4 illustrates an exemplary reaction cycle for the oxidation process, which includes separation of the oxygenate.
Figure 4:
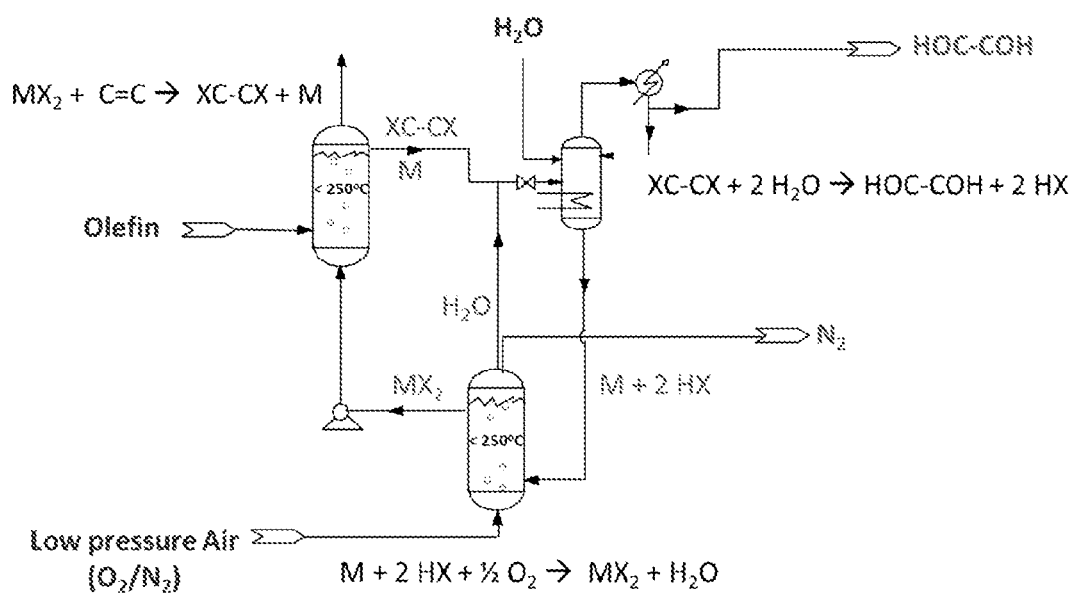

The solutions prepared according to Eq. 4 or Eq. 5 were reacted with ethylene in an apparatus similar to the schematic shown in FIG. 4 at room temperature to produce the trifluoroacetic (TFA) ester of ethylene glycol.

Figure 5:
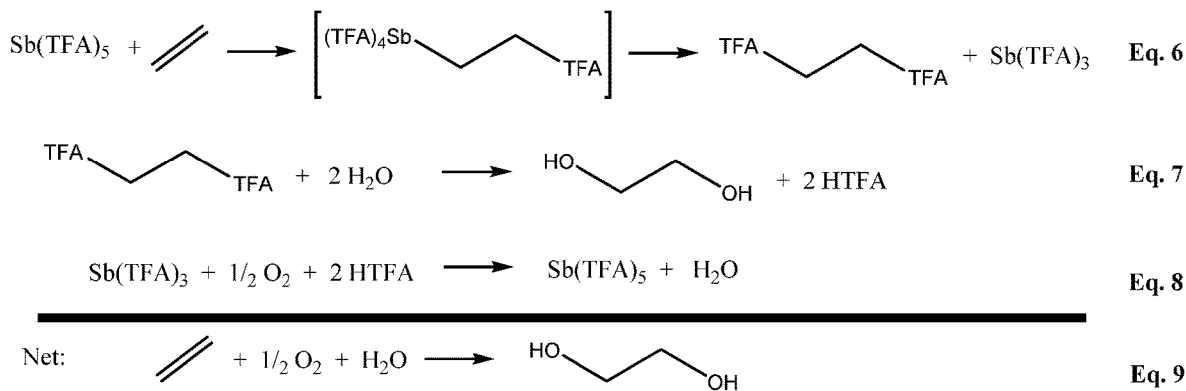
FIG. 5 is a proposed mechanism for the conversion of ethylene to ethylene glycol with an oxidizing electrophile.

FIG. 5 is a proposed mechanism of this process, which includes the addition of $(TFA)_4Sb^V$-TFA to the olefin (e.g., ethylene), to generate an oxidized intermediate. A reductive functionalization to generate the diester (e.g., ethylene glycol) and reduced $Sb(TFA)_3$ then follows. The TFA ester is hydrolyzed to form the ethylene glycol, and the $Sb(TFA)_3$ is reoxidized to form $Sb^V(TFA)_5$. The net reaction for this process is exemplified by Eq. 9 of FIG. 5.

EXAMPLE 2

This example demonstrates the pressure dependence on the reaction of $Sb^V(TFA)_5$ with $C_2H_4$ to form a trifluoroacetic (TFA) ester of ethylene glycol.

To generate $Sb^V(TFA)_5$, 124.6 mg (0.225 mmol) of [Sb(OMe)$_5$]2 was weighed out into a 10 mL Schlenk flask in an inert atmosphere glovebox. After removing the flask from the glovebox, under argon, the solid was dissolved in 1.125 mL of TFAA and stirred at room temperature for 30 minutes. TFAH (3.375 mL) was subsequently added to the mixture. The mixture was then stirred at room temperature for an additional 15 mins. This process generated a 50 mM solution of $Sb(TFA)_5$.

Next, 1 mL aliquots of the $Sb(TFA)_5$ solution were transferred to three separate 2 mL glass vials, all containing a stir bar. This step occurred in an inert atmosphere acid box. The vials were then plugged and placed in three separate 3 mL stainless steel pressure reactors. Afterward, the reactors were sealed and degassed by pressurizing to 500 psig Ar and purging (repeated three times). The reactors were then pressurized with the reaction gas (125 psig, 250 psig, and 500 psig of $C_2H_4$), purged, and re-pressurized three times. Following pressurization, the reactors were sealed with the reaction gas (125 psig, 250 psig, and 500 psig of $C_2H_4$) and placed into aluminum blocks, where the stir plate was then set to stir at 1000 rpm. The reactions were run for 40 minutes at room temperature, before they were quickly cooled with a dry ice/acetone bath. The gas was then released.

After opening the reactors, 250 μL of a 100 mM solution of 1,1,2,2-tetrachloroethane in TFAH/TFAA was added to each of the reaction solutions as an internal standard. Afterward, a capillary of $d_6$-benzene was added, and $^1$H-NMR spectra were subsequently taken with 20 second relaxation delays. The $^1$H-NMR spectra are referenced to the 1,1,2,2-tetrachloroethane (5.63 ppm). The product yields are provided in Table 1 and are based on added oxidant.

TABLE 1

| Entry | Pressure (psig) | EG(TFA)$_2$ (mM) | Yield (%) |
|---|---|---|---|
| 1 | 125 | 5.75 | 11.5 |
| 2 | 250 | 7.125 | 14.3 |
| 3 | 500 | 6.75 | 13.5 |

Figure 6:
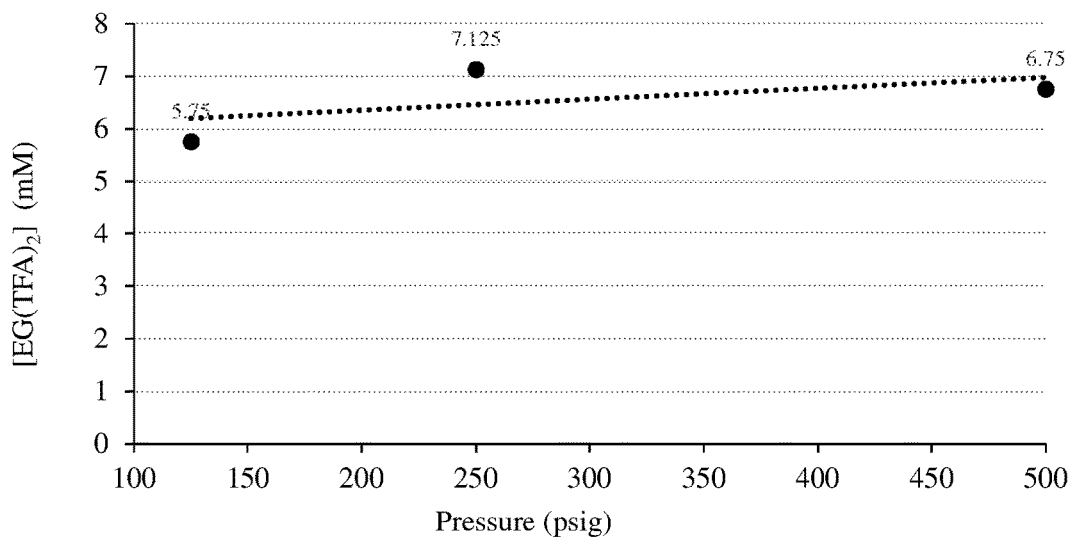
FIG. 6 shows the pressure dependence on the reaction of $Sb^V(TFA)_5$ with $C_2H_4$.

This example demonstrates that the desired TFA ester of ethylene glycol (EG(TFA)$_2$) is formed over a range of ethylene pressures (e.g., 125 psig, 250 psig, and 500 psig of $C_2H_4$). As shown in FIG. 6, the product yield appears to be independent of ethylene pressure in the reactor.

EXAMPLE 3

This example demonstrates the pressure-dependence on the reaction of $Sb^V(OAc)_5$ with $C_2H_4$.

To generate $Sb^V(OAc)_5$, 124.6 mg (0.225 mmol) of [Sb(OMe)$_5$]2 was weighed out into a 10 mL Schlenk flask in an inert atmosphere glovebox. After removing the flask from the glovebox, under argon, the solid was dissolved in 1.125 mL of acetic anhydride (AA) and stirred at room temperature for 30 minutes. Acetic acid (3.375 mL) was subsequently added to the mixture. The mixture was then stirred at room temperature for an additional 15 mins. This process generated a 50 mM solution of $Sb(OAc)_5$.

Next, 1 mL aliquots of the $Sb(OAc)_5$ solution were transferred to three separate 2 mL glass vials, all containing a stirbar. This step occurred in a purge box. The vials were then plugged and placed in three separate 3 mL stainless steel pressure reactors. Afterward, the reactors were sealed and degassed by pressurizing to 500 psig Ar and purging (repeated three times). The reactors were then pressurized with the reaction gas (125 psig, 250 psig, and 500 psig of $C_2H_4$), purged, and re-pressurized three times. Following pressurization, the reactors were sealed with the reaction gas (125 psig, 250 psig, and 500 psig of $C_2H_4$) and placed into aluminum blocks, where the stir plate was then set to stir at 1000 rpm. The reactions were run for 40 minutes at room temperature, before they were quickly cooled with a dry ice/acetone bath. The gas was then released.

The reaction with $Sb(OAc)_5$ generated the diacetate ester of ethylene glycol, similar to the TFA ester of ethylene glycol shown in Example 2.

EXAMPLE 4

This example demonstrates the oxidation of an alkene substrate in the presence of an oxidation composition containing a non-oxidizable liquid, an oxidizing electrophile, and optionally an additive.

The substrate (e.g., ethylene, 1-hexene, N-allylphthalimide, 1,5-hexadiene, 3-nitrostryene, 4-trifluoromethylstyrene, and 3,5-bis(trifluoromethyl)styrene) was dissolved in the corresponding non-oxidizable liquid (liquid species) to yield a 0.5 M solution. The oxidant (e.g., Tl(X)$_3$, Pb(X)$_4$, $C_6F_5I$(X)$_2$, Sb(X)$_3$ and $H_2O_2$, and Sb(X)$_6$) was dissolved in the corresponding liquid species to yield a 0.2 M solution. "X" is as defined in FIGS. 7A-7B. 2.0 mL of the oxidant solution was added to a 2-5 ml microwave vial equipped with a stir bar. The substrate solution (2.0 mL) was added to the microwave vial. The additives (if present) were added to the reaction and the crimp seal cap was sealed to the top of the vial. For gaseous substrates (e.g., ethylene), the reaction vial was charged with the gaseous substrate prior to sealing.

For the preparation of the $Sb(OAc)_3$ and $H_2O_2$ solution, the following procedure was followed. $Sb(OAc)_3$ and additives (except anhydrides) were dissolved in a solvent (10% less than total theoretical volume) in a vial at room temperature. The 50% $H_2O_2$ in $H_2O$ was added to the solution and stirred for 10 min. The anhydride was added, the vial was capped, and stirred for 10 min at room temperature. The solution was opened and solvent was added to achieve desired final volume to give the correct Sb concentration.

The vials were placed into a preheated aluminum block set to the appropriate temperature (25-180° C.). The reactions were stirred at temperature for 1 h. The vials were removed from the heat and cooled to room temperature. 1.0 ml of the solutions were added to a 1-dram vial and a standard was added to the solution. A sample of the solution was added to an NMR tube equipped with a capillary containing $d_6$-benzene. Quantitative NMR spectra were acquired for each sample. The results are set forth in FIGS. 7C-7D.

Figure 7C:
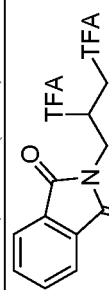
Figure 7C:
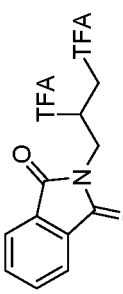
Figure 7C:
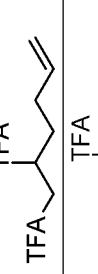
Figure 7C:

As is apparent from the results set forth in in FIGS. 7C-7D, the non-oxidizable liquids (liquid species) are not only stable to the reaction conditions, but also produce oxidizing compositions capable of oxidizing the alkene to the oxygenate (e.g., diester).

EXAMPLE 5

This example demonstrates the oxidation of propylene in the presence of an oxidation composition comprising a non-oxidizable liquid, an Sb(V) species, and an additive.

A reactor containing an Sb(V) species, sulfolane, and an additive was charged with propylene. The Sb(V) species used in this example was generated in situ by the addition of 50% hydrogen peroxide to an Sb(III) species and acetic anhydride in sulfolane. The solution was stirred at either 130° C., 150° C., 170° C., or 190° C. for 1 or 3 hours. Percent yield of the oxidation product, di-ester of 1,2-propanediol, was measured by 1H NMR spectroscopy, using characteristic peaks determined from authentic samples, by comparing relative peak ratios before oxidation and after the 1- or 3-hour heating period. Oxidation product yield is reported based on amount of hydrogen peroxide added to the reaction. The results are set forth in Table 2.

TABLE 2

| Entry | Additive | [Additive] (mM) | Temperature (° C.) | % Yield (based on Sb(V)) After 1 hr | % Yield (based on Sb(V)) After 3 hr |
|---|---|---|---|---|---|
| 1 | KOAc | 100 | 130-190 | <1% | <1% |
| 2 | KOMs | 100 | 130 | <1% | <10% |
| 3 | KOMs | 100 | 150 | <5% | 20% |
| 4 | KOMs | 100 | 170 | 20% | 40% |
| 5 | KOMs | 100 | 190 | 20% | 20% |

As is apparent from the results set forth in Table 2, the oxidizing composition also oxidizes propylene in the absence of a strong acid (see, for example, entries 4 and 5).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments can become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A process for oxidizing an alkene, comprising:
    (a) contacting an alkene, and
    (i) an oxidizing electrophile comprising a main group element selected from lead, antimony, mercury, tin, selenium, tellurium, arsenic, iodine, and bismuth in oxidized form, or
    (ii) an oxidant and a reduced form of the oxidizing electrophile,
    in a liquid medium comprising an oxygen acid and optionally one or more additives selected from a non-oxidizable liquid, a salt additive, a Lewis acid, and water, to provide, without the need for molecular oxygen, an oxygenate and a reduced form of the oxidizing electrophile; and
    (b) optionally separating the oxygenate and the reduced form of the oxidizing electrophile.

2. The process of claim 1, comprising (b) separating the oxygenate and the reduced form of the oxidizing electrophile.

3. The process of claim 1, further comprising (c) hydrolyzing the oxygenate to form an alcohol, a diol, a polyol with three or more hydroxyl groups, or a combination thereof.

4. The process of claim 3, wherein the hydrolysis step takes place in the presence of an acid.

5. The process of claim 3, wherein the hydrolysis step takes place in the presence of a base.

6. The process of claim 1, wherein the oxidizing electrophile comprises antimony, tellurium, arsenic, or bismuth.

7. The process of claim 1, wherein the oxidizing electrophile comprises at least one conjugate anion of an oxygen acid.

8. The process of claim 7, wherein the conjugate anion of the oxygen acid is an aliphatic carboxylate, heteroaliphatic carboxylate, aromatic carboxylate, heteroaromatic carboxylate, aliphatic sulfonate, heteroaliphatic sulfonate, aromatic sulfonate, heteroaromatic sulfonate, aliphatic phosphate, heteroaliphatic phosphate, aromatic phosphate, heteroaromatic phosphate, aliphatic borate, heteroaliphatic borate, aromatic borate, heteroaromatic borate, or a mixture thereof.

9. The process of claim 7, wherein the oxidizing electrophile further comprises at least one ligand with at least one electron-withdrawing group.

10. The process of claim 9, wherein the ligand with at least one electron-withdrawing group is selected from

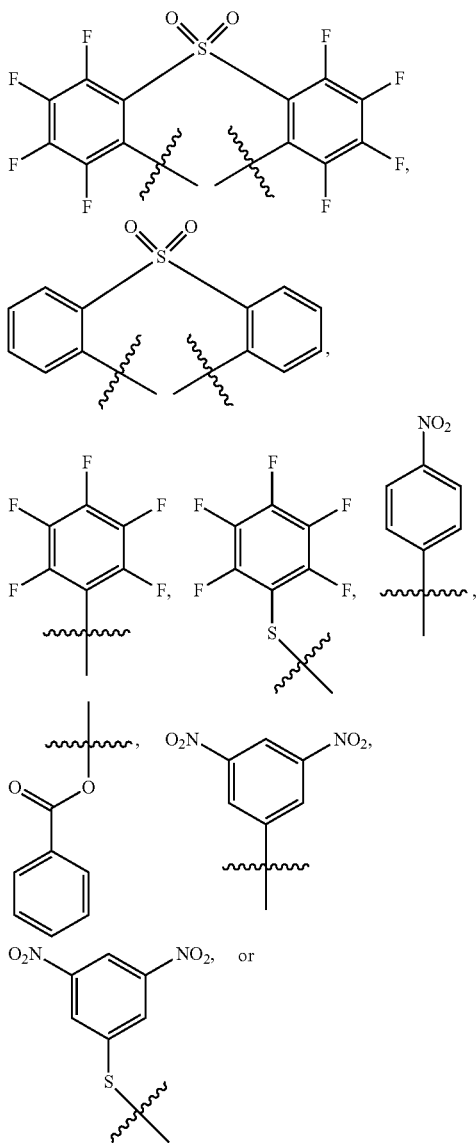

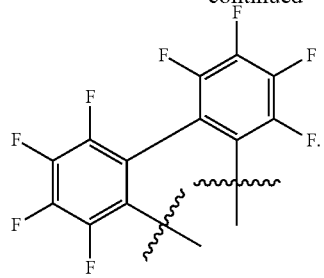

11. The process of claim 1, wherein the oxidizing electrophile has a formula $M^{+n}X_pL_q$, wherein M is a main group element cation in an oxidation state of n, X is the conjugate anion of an oxygen acid, L is a ligand, n is an integer from 2 to 6, p is an integer from 1 to 6, and q is an integer from 0 to 5.

12. The process of claim 1, wherein the oxidizing electrophile comprising a main group element in oxidized form is present in less than stoichiometric quantities relative to the oxygenate and acts as a catalyst.

13. The process of claim 12, further comprising (d) contacting the reduced form of the oxidizing electrophile and an oxidizing regeneration reagent to regenerate the oxidizing electrophile.

14. The process of claim 13, wherein the oxidizing regeneration reagent is a quinone, molecular oxygen, air, a peroxide, nitric oxide, nitrous oxide, nitric acid, a nitroxide, sulfur trioxide, ozone, or a combination thereof.

15. The process of claim 13, wherein step (d) is an electrochemical process.

16. The process of claim 14, wherein the reduced form of the oxidizing electrophile and the oxidizing regeneration reagent are contacted to regenerate the oxidizing electrophile in the presence of an oxidative regeneration catalyst.

17. The process of claim 16, wherein the oxidative regeneration catalyst comprises copper, silver, iron, cobalt, manganese, nickel, chromium, vanadium, or a combination thereof.

18. The process of claim 1, wherein the oxygen acid is aliphatic carboxylic acid, heteroaliphatic carboxylic acid, aromatic carboxylic acid, heteroaromatic carboxylic acid, aliphatic sulfonic acid, heteroaliphatic sulfonic acid, aromatic sulfonic acid, heteroaromatic sulfonic acid, aliphatic phosphonic acid, heteroaliphatic phosphonic acid, aromatic phosphonic acid, heteroaromatic phosphonic acid, boric acid, aliphatic boronic acid, heteroaliphatic boronic acid, aromatic boronic acid, heteroaromatic boronic acid, or a mixture thereof.

19. The process of claim 1, wherein all or a portion of the oxygen acid is added as an anhydride of the oxygen acid.

20. The process of claim 1, wherein the liquid medium comprises a non-oxidizable liquid selected from a fluorinated hydrocarbon, a sulfone, a deactivated arene, a deactivated aliphatic, a deactivated heteroarene, a deactivated heteroaliphatic, or a combination thereof, wherein the non-oxidizable liquid is substantially inert in the presence of the oxidizing electrophile.

21. The process of claim 1, wherein the liquid medium comprises a salt additive of formula $Q_aZ_b$, wherein Q is a cation, Z is a bridging oxide, a terminal oxide, a hydroxide, or a conjugate anion of an oxygen acid, a is an integer from 1 to 5, and b is an integer from 1 to 5, wherein a and b are the same or different and balance the oxidation states of Q and Z.

22. The process of claim 21, wherein Z is a conjugate anion of an oxygen acid that is one or more selected from an aliphatic carboxylate, heteroaliphatic carboxylate, aromatic carboxylate, heteroaromatic carboxylate, aliphatic sulfonate, heteroaliphatic sulfonate, aromatic sulfonate, heteroaromatic sulfonate, aliphatic phosphate, heteroaliphatic phosphate, aromatic phosphate, heteroaromatic phosphate, aliphatic borate, heteroaliphatic borate, aromatic borate, heteroaromatic borate, or a mixture thereof.

23. The process of claim 1, wherein the liquid medium comprises a Lewis acid.

* * * * *